United States Patent

Dombroski et al.

Patent Number: 6,166,064
Date of Patent: Dec. 26, 2000

[54] SULFONYL UREA DERIVATIVES AND THEIR USE IN THE CONTROL OF INTERLEUKIN-1 ACTIVITY

[75] Inventors: Mark Anthony Dombroski, Waterford; James Frederick Eggler, Stonington, both of Conn.

[73] Assignee: Pfizer Inc, New York, N.Y.

[21] Appl. No.: 09/341,782

[22] PCT Filed: Dec. 29, 1997

[86] PCT No.: PCT/IB97/01603

§ 371 Date: Jul. 16, 1999

§ 102(e) Date: Jul. 16, 1999

[87] PCT Pub. No.: WO98/32733

PCT Pub. Date: Jul. 30, 1998

Related U.S. Application Data

[60] Provisional application No. 60/036,979, Jan. 29, 1997.

[51] Int. Cl.[7] .................. A61K 31/335; A61K 31/40; A61K 31/18; C07D 319/06; C07C 273/00

[52] U.S. Cl. .................. 514/452; 514/418; 514/596; 514/602; 514/604; 514/605; 549/372; 549/373; 549/369; 548/484; 564/48; 564/89; 564/92

[58] Field of Search .................. 549/372, 369, 549/373; 514/452, 418, 596, 602, 604, 605; 548/484; 564/48, 89, 92

[56] References Cited

U.S. PATENT DOCUMENTS 4,586,950  5/1986  Pasteris ..................... 544/49

FOREIGN PATENT DOCUMENTS 9201684  2/1992  WIPO .
9308161  4/1993  WIPO .

OTHER PUBLICATIONS

ICI Australia, CA 114:122351, 1991.

*Primary Examiner*—Deborah C. Lambkin
*Attorney, Agent, or Firm*—Peter C. Richardson; Paul H. Ginsburg; Garth Butterfield

[57] ABSTRACT

A compound of formula (I)

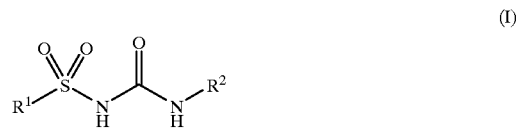

wherein $R^1$ and $R^2$ are as defined in the description, $R^2$ being an aromatic group, useful in the treatment and condition selected from the group consisting of the group meningitis and salpingitis, septic shock, disseminated intravascular coagulation, and/or adult respiratory distress syndrome, acute or chronic inflammation, arthritis, cholangitis, colitis, encephalitis, endocarditis, glomerulonephritis, hepatitis, myocarditis, pancreatitis, pericarditis, reperfusion injury, vasculitis, acute and delayed hypersensitivity, graft rejection, and graft-versus-host disease, auto-immune diseases including Type 1 diabetes mellitus and multiple sclerosis, periodonate diseases, interstitial pulmonary fibrosis, cirrhosis, systemic sclerosis, keloid formation tumors which produce IL-1 as an autocrine growth factor, cachexia, Alzeimer's disease, percussion injury, depression, atherosclerosis, osteoporosis in a mammal, including human.

13 Claims, No Drawings

SULFONYL UREA DERIVATIVES AND THEIR USE IN THE CONTROL OF INTERLEUKIN-1 ACTIVITY

The present application is a 371 application of International patent Application PCT/IB97/01603 filed Dec. 29, 1997 (which published as WO 98/32733), which was a continuation of United States Provisional Application 60/036979, filed Jan. 29, 1997.

BACKGROUND OF THE INVENTION

This invention relates to substituted urea derivatives useful in the treatment of inflammation in joints, central nervous system, gastorintestinal tract, endocardium, pericardium, lung, eyes, ears, skin and urogenital system. More particularly, this invention relates to aryl and heteroaryl substituted sulfonyl ureas that are useful inhibitors of interleukin-1α and interleukin-1β processing and release.

IL-1's status as an important mediator of inflammation is based on many studies demonstrating this cytokine's proinflammatory activity. In vivo these effects are manifest as stimulation of cartilage resorption, induction of leukocyte recruitment and the acute phase response, and the production of fever and a shock like state. The changes mediated by IL-1 binding to its receptor include regulation of adhesion molecules and chemokines, stimulation of metalloprotease synthesis, increased synthesis of cyclooxygenase-2 and phospholipase A2 thus increasing prostaglandin production, the induction of nitric oxide synthase thus increasing nitric oxide production and stimulation of IL-6 synthesis resulting in changes in the synthesis of acute phase proteins. Two distinct forms of IL-1 (IL-1α and IL-1β) are produced by monocytes and macrophages in response to inflammatory stimuli.

The initial translation product of human IL-1β is a 31 kDa polypeptide that is incompetent to bind to IL-1 receptors on target cells. To promote its biological activity, proIL-1β first must be cleaved by a thiol protease to generate a 17 kDa mature polypeptide species. This protease, interleukin-1 convertase (ICE), is a member of a novel family of cytosolic proteases that require an aspartic acid residue at the P1 subsite of their substrates. In contrast to proIL-1β, 31 kDa proIL-1α is competent to bind to IL-1 receptors; nonetheless, this cytokine also is processed to a 17 kDa species by a protease distinct from ICE.

Both forms of IL-1 are synthesized without signal sequences and, as a result, these cytokines accumulate within the cytoplasm of LPS activated monocytes and macrophages. Thus, unlike the majority of secreted cytokines that are processed via the traditional secretory apparatus of the cell involving the endoplasmic reticulum and Golgi apparatus, IL-1 must gain access to the extracellular compartment via a novel secretory pathway. The mechanistic elements of this pathway remain unknown. Recent studies, however, have demonstrated that synthesis of IL-1β is not coupled to its secretion. Agents that serve as a stimulus to promote IL-1β posttranslational processing (both proteolytic cleavage by ICE and release of the mature 17 kDa species) include ATP, cytolytic T-cells, and ionophores such as nigericin. Importantly, LPS-activated murine peritoneal macrophages in vivo also require a secondary stimulus to promote efficient release of mature IL-1β, and ATP was demonstrated to serve in this capacity. Thus, IL-1β production is highly regulated both in vitro and in vivo by requiring separate stimuli to promote transcription, translation, and posttranslational maturation/release.

Therapeutic approaches that seek to inhibit ICE as a means to regulate production of IL-1 are likely to be limited because ICE inhibitors: 1) do not block release of proIL-1β which could be processed extracellularly by other proteases to generate a mature biologically active cytokine species, and 2) do not decrease production of IL-1α by activated monocytes/macrophages. Therefore, a therapeutic approach that prevents activation of the posttranslational processing and release of IL-1 is likely to provide efficacy superior to that of an ICE inhibitor by blocking externalization of both cytokine species.

Mammalian cells capable of producing IL-1 include, but are not limited to, karatinocytes, endothelial cells, mesangial cells, thymic epithelial cells, dermal fibroblasts, chondrocytes, astrocytes, glioma cells, mononuclear phagocytes, granulocytes, T and B lymphocytes and NK cells.

The activities of interleukin-1 are many. Subcutaneous injection of IL-1 leads to fever, sleepiness, anorexia, generalized myalgias, arthralgias, headache, and, on increasing exposure, hypotension. Margination of neutrophils and maximal extravascular infiltration of the polymorphonuclear leukocytes (PMN) is also observed. IL-1 also stimulates chondrocytes to release matrix metalloproteases, resulting in the degradation of cartilage matrix.

Accordingly, disease states in which the IL-1 processing and release inhibitors of Formula 1 may be useful as therapeutic agents include, but are not limited to, infectious diseases where active infection exists at any body site, such as meningitis and salpingitis; complication of infections including septic shock, disseminated intravascular coagulation, and/or adult respiratory distress syndrome; acute or chronic inflammation due to antigen, antibody and/or complement deposition; inflammatory conditions including arthritis, cholangitis, colitis, encephalitis, endocarditis, glomerulonephritis, hepatitis, myocarditis, pancreatitis, pericarditis, reperfusion injury and vasculitis. Immune-based diseases which may be responsive to IL-1 processing and release inhibitors of Formula 1 include but are not limited to conditions involving T-cells and/or macrophages such as acute and delayed hypersensitivity, graft rejection, and graft-versus-host disease; auto-immune diseases including Type 1 diabetes mellitus and multiple sclerosis. IL-1processing and release inhibitors of Formula 1 may also be useful in the treatment of bone and cartilage resorption as well as diseases resulting in excessing deposition of extracellular matrix. Such diseases include periodonate diseases, interstitial pulmonary fibrosis, cirrhosis, systemic sclerosis and keloid formation. IL-1 processing and release inhibitors of Formula 1 may also be useful in treatment of certain tumors which produce IL-1 as an autocrin growth factor and in preventing the cachexia associated with certain tumors. IL-1 processing and release inhibitors of Formula 1 may also be useful in the treatment of neuronal diseases with an inflammatory component, including, but not limited to Alzheimers disease, depression and percussion injury. IL-1 processing and release inhibitors may also be useful in treating cardiovascular diseases in which recruitment of monocytes into the subendothelial space plays a role, such as the development of atherosclerotic placques.

SUMMARY OF THE INVENTION

The present invention relates to a compound of the formula

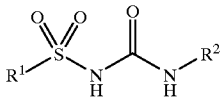
I or a pharmaceutically acceptable salt thereof, wherein $R^1$ $(C_1-C_6)$alkyl optionally substituted by $(C_1-C_6)$alkylamino, $(C_1-C_6)$alkylthio, $(C_1-C_6)$alkoxy, trifluoromethyl, $(C_6-C_{10})$aryl, $(C_5-C_9)$heteroaryl, $(C_6-C_{10})$arylamino, $(C_6-C_{10})$arylthio, $(C_6-C_{10})$aryloxy, $(C_5-C_9)$heteroarylamino, $(C_5-C_9)$heteroarylthio, $(C_5-C_9)$heteroaryloxy, $(C_6-C_{10})$aryl$(C_6-C_{10})$aryl, $(C_3-C_6)$cycloalkyl, hydroxy$(C_1-C_6)$alkyl, $(C_1-C_6)$alkyl(hydroxymethylene, piperazinyl, $(C_6-C_{10})$aryl$(C_1-C_6)$alkoxy, $(C_5-C_9)$heteroaryl$(C_1-C_6)$alkyl(hydroxymethylene), piperazinyl, $(C_1-C_6)$acylthio, $(C_1-C_6)$acyloxy, $(C_1-C_6)$alkylsulfinyl, $(C_6-C_{10})$arylsulfinyl, $(C_1-C_6)$alkylsulfonyl, $(C_6-C_{10})$arylsulfonyl, amino, $(C_1-C_6)$alkylamino or $((C_1-C_6)$alkyl$)_2$amino; or $R^1$ and $R^2$ are each independently a group of the formula

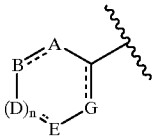
II wherein the broken lines represent optional double bonds;

n is 0, 1, 2 or 3;

A, B, D, E and G are each independently oxygen, sulfur, nitrogen or $CR^5 R^6$ wherein $R^5$ and $R^6$ are each independently selected from hydrogen, $(C_1-C_6)$alkyl optionally substituted by one or two groups selected from $(C_1-C_6)$alkylamino, $(C_1-C_6)$alkylthio, $(C_1-C_6)$alkoxy, hydroxy, cyano, perfluoro$(C_1-C_6)$alkyl, $(C_6-C_{10})$aryl, $(C_5-C_9)$heteroaryl, $(C_6-C_{10})$arylamino, $(C_6-C_{10})$arylthio, $(C_6-C_{10})$aryloxy wherein the aryl group is optionally substituted by $(C_1-C_6)$alkoxy, $(C_1-C_6)$acyl, carboxy, hydroxy or halo; $(C_5-C_9)$heteroarylamino, $(C_5-C_9)$heteroarylthio, $(C_5-C_9)$heteroaryloxy, $(C_6-C_{10})$aryl$(C_6-C_{10})$aryl, $(C_3-C_6)$cycloalkyl, hydroxy, piperazinyl, $(C_6-C_{10})$aryl$(C_1-C_6)$alkoxy, $(C_5-C_9)$heteroaryl$(C_1-C_6)$alkoxy, $(C_1-C_6)$acylamino, $(C_1-C_6)$acylthio, $(C_1-C_6)$acyloxy, $(C_1-C_6)$alkylsulfinyl, $(C_6-C_{10})$arylsulfinyl, $(C_1-C_6)$alkylsulfonyl, $(C_6-C_{10})$arylsulfonyl, amino, $(C_1-C_6)$alkylamino or $((C_1-C_6)$alkyl$)_2$amino; halo, cyano, amino, hydroxy, perfluoro$(C_1-C_6)$alkyl, perfluoro$(C_1-C_6)$alkoxy, $(C_2-C_6)$alkenyl, carboxy$(C_2-C_6)$alkenyl, $(C_2-C_6)$alkynyl, $(C_1-C_6)$alkylamino, $((C_1-C_6)$alkyl$)_2$amino, $(C_1-C_6)$alkylsulfonylamido, $(C_1-C_6)$alkylsulfinyl, aminosulfonyl, $(C_1-C_6)$alkylaminosulfonyl, $((C_1-C_6)$alkyl$)_2$aminosulfonyl, $(C_1-C_6)$alkylthio, $(C_1-C_6)$alkoxy, perfluoro$(C_1-C_6)$alkyl, $(C_6-C_{10})$aryl, $(C_5-C_9)$heteroaryl, $(C_6-C_{10})$arylamino, $(C_6-C_{10})$arylthio, $(C_6-C_{10})$aryl$(C_1-C_6)$alkoxy, $(C_5-C_9)$heteroarylamino, $(C_5-C_9)$heteroarylthio, $(C_5-C_9)$heteroaryloxy, $(C_3-C_6)$cycloalkyl, $(C_1-C_6)$alkyl(hydroxymethylene), piperidyl, pyridinyl, thienyl, furanyl, $(C_1-C_6)$alkylpiperidyl, $(C_1-C_6)$acylamino, $(C_1-C_6)$acylthio, $(C_1-C_6)$acyloxy, $R^7(C_1-C_6)$alkyl wherein $R^7$ is $(C_1-C_6)$acylpiperazino, $(C_6-C_{10})$arylpiperazino, $(C_5-C_9)$heteroarylpiperazino, $(C_1-C_6)$alkylpiperazino, $(C_6-C_{10})$aryl$(C_1-C_6)$alkylpiperazino, $(C_5-C_9)$heteroaryl$(C_1-C_6)$alkylpiperazino, morpholino, thiomorpholino, piperidino, pyrrolidino, piperidyl, $(C_1-C_6)$alkylpiperidyl, $(C_6-C_{10})$arylpiperidyl, $(C_5-C_9)$heteroarylpiperidyl, $(C_1-C_6)$alkylpiperidyl$(C_1-C_6)$alkyl, $(C_6-C_{10})$arylpiperidyl$(C_1-C_6)$alkyl, $(C_5-C_9)$heteroarylpiperidyl$(C_1-C_6)$alkyl or $(C_1-C_6)$acylpiperidyl;

or a group of the formula

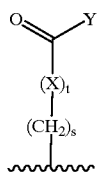
III wherein s is 0 to 6;

t is 0 or 1;

X is oxygen or $NR^8$ wherein $R^8$ is hydrogen, $(C_1-C_6)$alkyl or $(C_3-C_7)$cycloalkyl$(C_1-C_6)$alkyl;

Y is hydrogen, hydroxy, $(C_1-C_6)$alkyl, optionally substituted by halo, hydroxy or cyano; $(C_1-C_6)$alkoxy, cyano, $(C_2-C_6)$alkynyl, $(C_6-C_{10})$aryl wherein the aryl group is optionally substituted by halo, hydroxy, carboxy, $(C_1-C_6)$alkyl, $(C_1-C_6)$alkoxy; perfluoro$(C_1-C_6)$alkyl, $(C_1-C_6)$alkoxy$(C_1-C_6)$alkyl or $NR^9R^{10}$ wherein $R^9$ and $R^{10}$ are each independently selected from the group consisting of hydrogen, $(C_1-C_6)$alkyl optionally substituted by $(C_1-C_6)$alkylpiperidyl, $(C_6-C_{10})$arylpiperidyl, $(C_5-C_9)$heteroarylpiperidyl, $(C_6-C_{10})$aryl, $(C_5-C_9)$heteroaryl or $(C_3-C_6)$cycloalkyl; piperidyl, $(C_1-C_6)$alkylpiperidyl, $(C_6-C_{10})$arylpiperidyl, $(C_5-C_9)$heteroarylpiperidyl, $(C_1-C_6)$acylpiperidyl, $(C_6-C_{10})$aryl, $(C_5-C_9)$heteroaryl, $(C_3-C_6)$cycloalkyl, $R^{11}$ $(C_2-C_6)$alkyl, $(C_1-C_5)$alkyl$(CHR^{11})(C_1-C_6)$alkyl wherein $R^{11}$ is hydroxy, $(C_1-C_6)$acyloxy, $(C_1-C_6)$alkoxy, piperazino, $(C_1-C_6)$acylamino, $(C_1-C_6)$alkylthio, $(C_6-C_{10})$arylthio, $(C_1-C_6)$alkylsulfinyl, $(C_6-C_{10})$arylsulfinyl, $(C_1-C_6)$alkylsulfonyl, $(C_6-C_{10})$arylsulfonyl, amino, $(C_1-C_6)$alkylamino, $((C_1-C_6)$alkyl$)_2$amino, $(C_1-C_6)$acylpiperazino, $(C_1-C_6)$alkylpiperazino, $(C_6-C_{10})$aryl$(C_1-C_6)$alkylpiperazino, $(C_5-C_9)$heteroaryl$(C_1-C_6)$alkylpiperazino, morpholino, thiomorpholino, piperidino or pyrrolidino; $R^{12}(C_1-C_6)$alkyl, $(C_1-C_5)$alkyl$(CHR^{12})(C_1-C_6)$alkyl wherein $R^{12}$ is piperidyl or $(C_1-C_6)$alkylpiperidyl; and $CH(R^{13})COR^{14}$ wherein $R^{14}$ is as defined below and $R^{13}$ is hydrogen, $(C_1-C_6)$alkyl, $(C_6-C_{10})$aryl$(C_1-C_6)$alkyl, $(C_5-C_9)$heteroaryl$(C_1-C_5)$alkyl, $(C_1-C_6)$alkylthio$(C_1-C_6)$alkyl, $(C_6-C_{10})$arylthio$(C_1-C_6)$alkyl, $(C_1C_6)$alkylsulfinyl$(C_1-C_6)$alkyl, $(C_6-C_{10})$arylsulfinyl$(C_1-C_6)$alkyl, $(C_1-C_6)$alkylsulfonyl$(C_1-C_6)$alkyl, $(C_6-C_{10})$arylsulfonyl$(C_1-C_6)$alkyl, hydroxy$(C_1-C_6)$alkyl, amino$(C_1-C_6)$alkyl, $(C_1-C_6)$alkylamino$(C_1-C_6)$alkyl, $((C_1-C_6)$alkylamino$)_2(C_1-C_6)$alkyl, $R^{15}R^{16}NCO(C_1-C_6)$alkyl or $R^{15}OCO(C_1-C_6)$alkyl wherein $R^{15}$ and $R^{16}$ are each independently selected from the group consisting of hydrogen, $(C_1–C_6)$alkyl, $(C_6–C_{10})$aryl$(C_1–C_6)$alkyl and $(C_5–C_9)$heteroaryl$(C_1–C_6)$alkyl; and $R^{14}$ is $R^{17}O$ or $R^{17}R^{18}N$ wherein $R^{17}$ and $R^{18}$ are each independently selected from the group consisting of hydrogen, $(C_1–C_6)$alkyl, $(C_6–C_{10})$aryl$(C_1–C_6)$alkyl and $(C_5–C_9)$heteroaryl$(C_1–C_6)$alkyl;

or a group of the formula

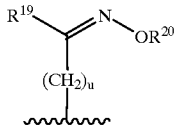

IV wherein u is 0, 1 or 2;

$R^{19}$ is hydrogen, $(C_1–C_6)$alkyl or perfluoro$(C_1–C_6)$alkyl;

$R^{20}$ is hydrogen, $(C_1–C_6)$alkyl, $(C_1–C_6)$carboxyalkyl or $(C_6–C_{10})$aryl$(C_1–C_6)$alkyl;

or a group of the formula

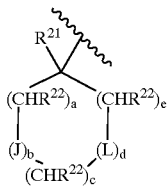

V wherein a is 0, 1 or 2;
b is 0 or 1;
c is 1, 2 or 3;
d is 0 or 1;
e is 0, 1 or 2;
J and L are each independently oxygen or sulfur;
$R^{21}$ is hydrogen, hydroxy, fluoro, $(C_1–C_6)$alkyl, $(C_1–C_6)$alkoxy, halo$(C_1–C_6)$alkyl, amino, $(C_1–C_6)$acylamino or $NR^{26}R^{27}$ wherein $R^{26}$ and $R^{27}$ are each independently selected from hydrogen, $(C_1–C_6)$alkyl or $(C_6–C_{10})$aryl; and
$R^{22}$ is hydrogen, $(C_1–C_6)$alkyl optionally by hydroxy, halo, $(C_1–C_6)$alkylthio, $(C_1–C_6)$alkylsulfinyl or $(C_1–C_6)$alkylsulfonyl;

or when n is 1 and B and D are both $CR^5$, the two $R^5$ groups may be taken together with the carbons to which they are attached to form a group of the formula

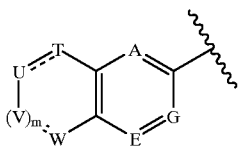

VI wherein the broken lines represent optional double bonds;
m is 0 or 1; and
T, U, V and W are each independently oxygen, sulfur, CO, nitrogen or $CR^5R^6$ wherein $R^5$ and $R^6$ are as defined above;
or when A and B, or when n is 1 and B and D, or D and E, or E and G, are both $CR^5$, the two $R^5$ groups may be taken together with the adjacent carbons to which they are attached to form a $(C_5–C_6)$cycloalkyl group optionally substituted by hydroxy or a benzo group;

or when n is 1 and D and E are both $CR^5$, the two $R^5$ groups may be taken together with the adjacent carbons to which they are attached to form a group of the formula

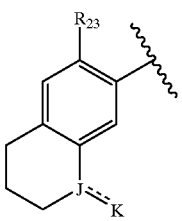

VII wherein the broken line represents an optional double bond;
$R^{23}$ is hydrogen, $(C_1–C_6)$alkyl, halo, amino or $(C_1–C_6)$alkoxy;
J is C or SO;
K is oxygen, $NR^{24}$ wherein $R^{24}$ is hydroxy, $(C_1–C_6)$alkoxy or $(C_6–C_{10})$aryl$(C_1–C_6)$alkoxy; or hydroxy;
or $R^{25}SO_2$ wherein $R^{25}$ is defined as $R^1$ above or $(C_3–C_7)$cycloalkylamino; and
with the proviso that the groups of formulas II and VI cannot have two oxygens, two sulfurs or an oxygen and sulfur defined in adjacent positions;
with the proviso that $R^2$ must be aromatic;
with the proviso that when either a or e is 0, the other must be 1;
with the proviso that when b and d are 1, the sum of a, c and e cannot be 6 or 7; and
with the proviso that when A, B, D, E, G, T, U, V and W represent an $sp^2$ carbon, $R^6$ does not exist.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined above.

The term "aryl", as used herein, unless otherwise indicated, includes an organic radical derived from an aromatic hydrocarbon by removal of one hydrogen, such as phenyl or naphthyl, optionally substituted by 1 to 3 substituents selected from the group consisting of fluoro, chloro, trifluoromethyl, $(C_1–C_6)$alkoxy, $(C_6–C_{10})$aryloxy, trifluoromethoxy, difluoromethoxy and $(C_1–C_6)$alkyl.

The term "heteroaryl", as used herein, unless otherwise indicated, includes an organic radical derived from an aromatic heterocyclic compound by removal of one hydrogen, such as pyridyl, furyl, pyroyl, thienyl, isothiazolyl, imidazolyl, binzimadazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl, optionally substituted by 1 or 2 substituents selected from the group consisting of fluoro, chloro, trifluoromethyl, $(C_1–C_6)$alkoxy, $(C_6–C_{10})$aryloxy, trifluoromethoxy, difluoromethoxy and $(C_1–C_6)$alkyl.

The term "acyl", as used herein, unless otherwise indicated, includes a radical of the general formula RCO wherein R is alkyl, alkoxy, aryl, arylalkyl or arylalkyloxy and the terms "alkyl" or "aryl" are as defined above.

The term "acyloxy", as used herein, includes O-acyl groups wherein "acyl" is defined above.

Preferred compounds of formula I include those wherein $R^1$ is a group of the formula

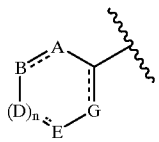

II wherein the broken lines represent double bonds;

n is 0 or 1;

A is $CR^5$ wherein $R^5$ is hydrogen or halo;

B and E are both independently $CR^5$ wherein $R^5$ is hydrogen cyano, halo, $(C_1-C_6)$alkyl optionally substituted by one or two hydroxy; $(C_3-C_7)$cycloalkylaminosulfonyl, $(C_1-C_6)$alkylaminosulfonyl, or a group of the formula

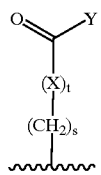

III wherein s is 0;

t is 0; and

Y is hydrogen, $(C_1-C_6)$alkyl optionally substituted by halo; or $(C_1-C_6)$alkoxy$(C_1-C_6)$alkyl;

or a group of the formula

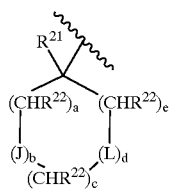

V wherein a is 0 or 1;

b is 0 or 1;

c is 1 or 2;

d is 0 or 1;

e is 0 or 1;

J and L are each independently oxygen or sulfur;

$R^{21}$ is hydrogen, hydroxy or $(C_1-C_6)$alkyl optionally substituted by halo; and $R^{22}$ is hydrogen or $(C_1-C_6)$alkyl optionally substituted by hydroxy, halo, $(C_1-C_6)$alkylthio, $(C_1-C_6)$alkylsulfinyl or $(C_1-C_6)$alkylsulfonyl;

or a group of the formula

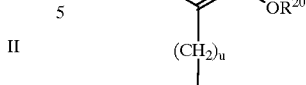

IV wherein u is 0 or 1;

$R^{19}$ is $(C_1-C_6)$alkyl or trifluoromethyl; and $R^{20}$ is hydrogen;

D is $CR^5$ wherein $R^5$ is hydrogen, $(C_1-C_6)$alkyl or halo;

G is $CR^5$ wherein $R^5$ is oxygen, sulfur or $CR^5$ wherein $R^5$ is hydrogen or halo;

or when n is 1 and B and D are both $CR^5$, the two $R^5$ groups may be taken together with the carbons to which they are attached to form a group of the formula

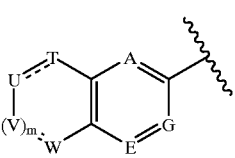

VI wherein the broken lines represent double bonds;

m is 0;

T is oxygen, nitrogen or $CR^5$ wherein $R^5$ is hydrogen;

U is CO or $CR^5$ wherein $R^5$ is hydrogen; and

W is nitrogen or $CR^5$ wherein $R^5$ is hydrogen;

or when n is 1 and D and E are both $CR^5$, the two $R^5$ groups may be taken together with the adjacent carbons to which they are attached to form a group of the formula

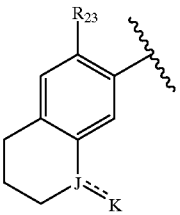

VII wherein the broken line represents an optional double bond;

$R^{23}$ is hydrogen or $(C_1-C_6)$alkyl;

J is C or SO

K is oxygen, $NR^{24}$ wherein $R^{24}$ is hydroxy; or hydroxy.

Other preferred compounds of formula I include those wherein $R^2$ is a group of the formula

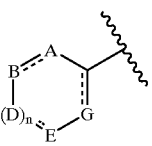

II wherein the broken lines represent optional double bonds;

n is 1;

A is $CR^5$ wherein $R^5$ is halo or $(C_1-C_6)$alkyl;

B is $CR^5$ wherein $R^5$ is hydrogen or halo;

D is $CR^5$ wherein $R^5$ is hydrogen, halo, cyano or a group of the formula

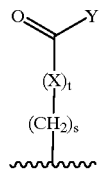

III wherein s is 0;

t is 0; and

Y is $NH_2$;

E is $CR^5$ wherein $R^5$ is hydrogen or halo; and

G is $CR^5$ wherein $R^5$ is halo or $(C_1-C_6)$alkyl;

or when A and B, or E and G, are both $CR^5$, the two $R^5$ groups may be taken together with the adjacent carbons to which they are attached to form a $(C_6-C_6)$cycloalkyl group.

Other preferred compounds of formula I include those wherein $R^1$ is a group of the formula

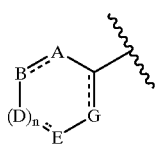

II wherein the broken lines represent double bonds;

n is 0 or 1;

A is $CR^5$ wherein $R^5$ is hydrogen or halo;

B and E are both independently $CR^5$ wherein $R^5$ is hydrogen cyano, halo, $(C_1-C_6)$alkyl optionally substituted by one or two hydroxy; $(C_3-C_7)$cycloalkylaminosulfonyl, $(C_1-C_6)$alkylaminosulfonyl, or a group of the formula

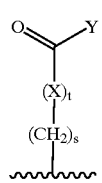

III wherein s is 0;

t is 0; and

Y is hydrogen, $(C_1-C_6)$alkyl optionally substituted by halo; or $(C_1-C_6)$alkoxy$(C_1-C_6)$alkyl;

or a group of the formula

V wherein a is 0 or 1;

b is 0 or 1;

c is 1 or 2;

d is 0 or 1;

e is 0 or 1;

J and L are each independently oxygen or sulfur;

$R^{21}$ is hydrogen, hydroxy or $(C_1-C_6)$alkyl optionally substituted by halo; and $R^{22}$ is hydrogen or $(C_1-C_6)$alkyl optionally substituted by hydroxy, halo, $(C_1-C_6)$alkylthio, $(C_1-C_6)$alkylsulfinyl or $(C_1-C_6)$alkylsulfonyl;

or a group of the formula

IV wherein u is 0 or 1;

$R^{19}$ is $(C_1-C_6)$alkyl or trifluoromethyl; and $R^{20}$ is hydrogen;

D is $CR^5$ wherein $R^5$ is hydrogen, $(C_1-C_6)$alkyl or halo;

G is $CR^5$ wherein $R^5$ is oxygen, sulfur or $CR^5$ wherein $R^5$ is hydrogen or halo;

or when n is 1 and B and D are both $CR^5$, the two $R^5$ groups may be taken together with the carbons to which they are attached to form a group of the formula

VI wherein the broken lines represent double bonds;

m is 0;

T is oxygen, nitrogen or $CR^5$ wherein $R^5$ is hydrogen;

U is CO or $CR^5$ is hydrogen; and

W is nitrogen or $CR^5$ wherein $R^5$ is hydrogen;

or when n is 1 and D and E are both $CR^5$, the two $R^5$ groups may be taken together with the adjacent carbons to which they are attached to form a group of the formula

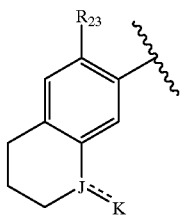

wherein the broken line represents an optional double bond;

R²³ is hydrogen or (C₁–C₆)alkyl;

J is C or SO

K is oxygen, NR²⁴ wherein R²⁴ is hydroxy; or hydroxy; and

R² is a group of the formula

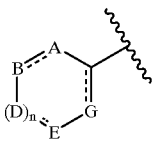

wherein the broken lines represent optional double bonds;

n is 1;

A is CR⁵ wherein R⁵ is halo or (C₁–C₆)alkyl;

B is CR⁵ wherein R⁵ is hydrogen or halo;

D is CR⁵ wherein R⁵ is hydrogen, halo, cyano or a group of the formula

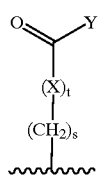

wherein s is 0;

t is 0; and

Y is NH₂;

E is CR⁵ wherein R⁵ is hydrogen or halo; and

G is CR⁵ wherein R⁵ is halo or (C₁–C₆)alkyl;

or when A and B, or E and G, are both CR⁵, the two R⁵ groups may be taken together with the adjacent carbons to which they are attached to form a (C₅–C₆)cycloalkyl group.

Specific preferred compounds of formula I include the following:

1-(4-Chloro-2,6-diisopropyl-phenyl)-3-[3-(1-hydroxy-1-methyl-ethyl)-benzenesulfonyl]-urea;

1-(1,2,3,5,6,7-Hexahydro-s-indacen-4-yl)-3-[4-(1-hydroxy-1-methyl-ethyl)-furan-2-sulfonyl]-urea;

1-(1,2,3,5,6,7-Hexahydro-4-aza-s-indacen-8-yl)-3-[4-(1-hydroxy-1-methyl-ethyl)-furan-2-sulfonyl]-urea;

1-(1,2,3,5,6,7-Hexahydro-s-indacen-4-yl)-3-[4-(1-hydroxy-1-methyl-ethyl)-thiophene-2-sulfonyl]-urea;

1-(4-[1,3]Dioxolan-2-yl-furan-2-sulfonyl)-3-(1,2,3,5,6,7-hexahydro-s-indacen-4-yl)-urea;

1-(2,6-Diisopropyl-phenyl)-3-[4-(1-hydroxy-1-methyl-ethyl)-furan-2-sulfonyl]-urea;

(1-(2,6-Diisopropyl-phenyl)-3-[4-(1-hydroxy-1-methyl-ethyl)-thiophene-2-sulfonyl]-urea;

1-(4-Acetyl-thiophene-2-sulfonyl)-3-(1,2,3,5,6,7-hexahydro-s-indacen-4-yl)-urea;

1-(1H-Benzoimidazole-5-sulfonyl)-3-(1,2,3,5,6,7-hexahydro-s-indacen-4-yl)-urea;

1-(1,2,3,5,6,7-Hexahydro-s-indacen-4-yl)-3-[4-(1-hydroxy-1-methyl-ethyl)-thiophene-2-sulfonyl]-urea;

1-(8-Chloro-1,2,3,5,6,7-hexahydro-s-indacen-4-yl)-3-[4-(1-hydroxy-1-methyl-ethyl)-furan-2-sulfonyl]-urea;

1-(4-Acetyl-furan-2-sulfonyl)-3-(1,2,3,5,6,7-hexahydro-s-indacen-4-yl)-urea;

1-(8-Fluoro-1,2,3,5,6,7-hexahydro-s-indacen-4-yl)-3-[4-(1-hydroxy-1-methyl-ethyl)-furan-2-sulfonyl]-urea;

1-(4-Fluoro-2,6-diisopropyl-phenyl)-3-[3-(1-hydroxy-1-methyl-ethyl)-benzenesulfonyl]-urea;

1-(6-Fluoro-1H-benzoimidazole-5-sulfonyl)-3-(1,2,3,5,6,7-hexahydro-s-indacen-4-yl)-urea;

1-(4-Chloro-2,6-diisopropyl-phenyl)-3-(1H-indole-6-sulfonyl)-urea;

1-(4-Chloro-2,6-diisopropyl-phenyl)-3-(5-fluoro-1H-indole-6-sulfonyl)-urea;

1-[1,2,3,5,6,7-Hexahydro-s-indacen-u-yl)-3-(1H-indole-6-sulfonyl)-urea;

1-(5-Fluoro-1H-indole-6-sulfonyl)-3-(1,2,3,5,6,7-hexahydro-5-indacen-4yl)-urea;

1-[4-Chloro-2,6-diisopropyl-phenyl]-3-[2-fluoro-5-(2-methyl-(1,3)dioxolan-2-yl)-benzenesulfonyl]-urea;

3-[3-[4-Chloro-2,6-diisopropyl-phenyl]-ureidosulfonyl]-N-methylbenzenesulfonamide;

1-[2-Fluoro-5-(2-methyl-(1,3)dioxolan-2-yl)benzenesulfonyl]-1,2,3,5,6,7-hexahydro-indacen-4-yl)-urea; and 3-[3-(1,2,3,5,6,7-Hexahydro-S-indacen-4-yl)-ureidosulfonyl]-N-methyl-benzenesulfonamide.

The present invention also relates to a pharmaceutical composition for the treatment of meningitis and salpingitis, septic shock, disseminated intravascular coagulation, and/or adult respiratory distress syndrome, acute or chronic inflammation, arthritis, cholangitis, colitis, encephalitis, endocarditis, glomerulonephritis, hepatitis, myocarditis, pancreatitis, pericarditis, reperfusion injury, vasculitis, acute and delayed hypersensitivity, graft rejection, and graft-versus-host disease, auto-immune diseases including Type 1 diabetes mellitus and multiple sclerosis, periodonate diseases, interstitial pulmonary fibrosis, cirrhosis, systemic sclerosis, keloid formation, tumors which produce IL-1 as an autocrine growth factor, cachexia, Alzheimers disease, percussion injury, depression, atherosclerosis (including cardiomyopathy, myocarditis and heart failure) and osteoporosis in a mammal, including a human, comprising administering an amount of a compound of formula I or a pharmaceutically acceptable salt thereof, effective in such treatments or inhibition and a pharmaceutically acceptable carrier.

The present invention also relates to a method for treating a condition selected from the group consisting of meningitis and salpingitis, septic shock, disseminated intravascular coagulation, and/or adult respiratory distress syndrome, acute or chronic inflammation, arthritis, cholangitis, colitis, encephalitis, endocarditis, glomerulonephritis, hepatitis, myocarditis, pancreatitis, pericarditis, reperfusion injury, vasculitis, acute and delayed hypersensitivity, graft rejection, and graft-versus-host disease, auto-immune diseases including Type 1 diabetes mellitus and multiple sclerosis, periodonate diseases, interstitial pulmonary fibrosis, cirrhosis, systemic sclerosis, keloid formation, tumors which produce IL-1 as an autocrine growth factor, cachexia, Alzheimers disease, percussion injury, depression, atherosclerosis (including cardiomyopathy, myocarditis and heart failure) and osteoporosis in a mammal, including a human, comprising administering to said mammal an amount of a compound of formula I or a pharmaceutically acceptable salt thereof, effective in treating such a condition.

DETAILED DESCRIPTION OF THE INVENTION

The following reaction Schemes illustrate the preparation of the present invention. Unless otherwise indicated in A, B, D, E and G in the reaction Schemes and the discussion that follow are defined as above.

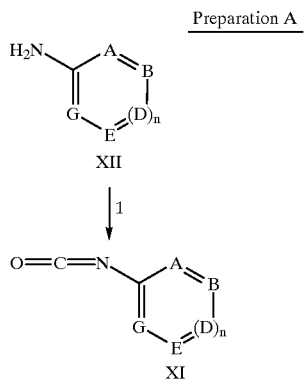

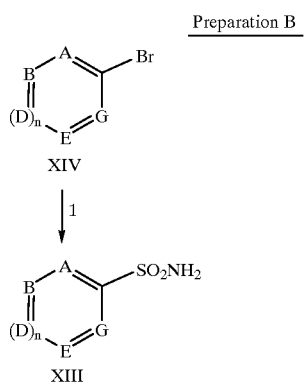

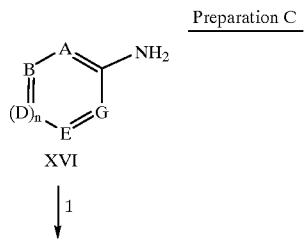

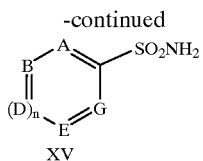

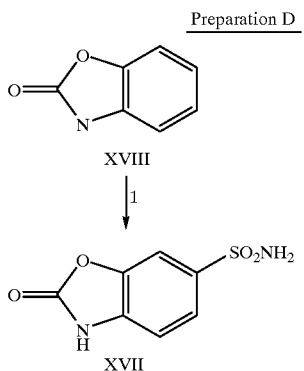

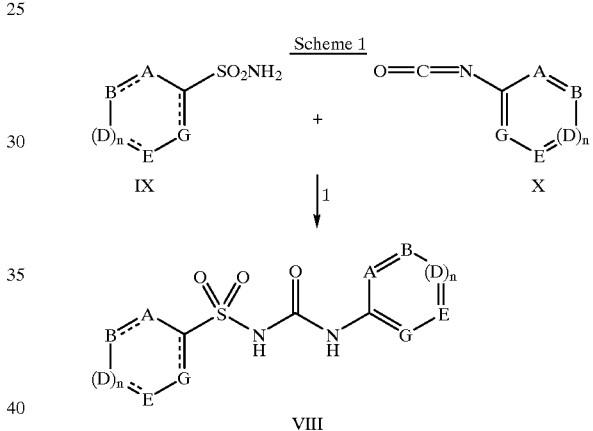

In reaction 1 of Preparation A, the compound of formula XII is converted to the corresponding isocyanate compound of formula XI by reacting XII with triphosgene in the presence of a base, such as triethylamine, diisopropylethylamine or 1,8-diazabicyclo[5,4,0]undec-7-ene, and a aprotic solvent, such as tetrahydrofuran, benzene or methylene chloride. The mixture is stirred and heated to reflux for a time period between about 1 hour to about 3 hours, preferably about 2 hours.

In reaction 1 of Preparation B, the compound of formula XIV is converted to the corresponding sulfonamide compound of formula XIII by adding an alkyllithium, such as n-butyl, sec-butyl or tert-butyl lithium, to a stirred solution of XIV in a polar solvent, such as tetahydrofuran, at a temperature between about −70° C. to about −85° C., preferably about −78° C. After approximately 15 minutes, liquefied sulfur dioxide is added to the reaction mixture so formed, stirred at approximately −78° C. for 5 minutes and then warmed to room temperature for a time period between about 1 hour to about 3 hours, preferably about 2 hours. The mixture is then (a) concentrated in vacuo, and treated with either a chlorinating reagent, such as N-chloro-succinimide in a polar solvent, such as methylene chloride, followed by treatment with gasous or aqueous ammonia or (b) treated with hydroxylamine o-sulfonic acid in water in the presence of a buffer, such as sodium acetate.

In reaction 1 of Preparation C, the compound of formula XVI is converted to the corresponding sulfonamide compound of formula XV by adding a solution of sodium nitrate in water to a stirred solution of XVI in a mixture acetic acid and hydrochloric acid. Acetic acid saturated with sulfur dioxide gas is then added followed by cuprous chloride. The reaction mixture so formed is stirred at a temperature between about −10° C. to about 10° C., preferably about 0° C., for a time period between about 1 hour to about 3 hours, preferably about 2 hours. The resulting sulfonyl chloride is then treated with gasous or aqueous ammonia bubbled through a solution of the sulfonyl chloride in an aprotic solvent, such as methylene chloride or ether.

In reaction 1 of Preparation D, the compound of formula XVIII is converted to the corresponding sulfonamide compound of formula XVII by reacting XVIII with chlorosulfonic acid in a polar aprotic solvent, such as chloroform at a temperature between about −10° C. to about 10° C., preferably about 0° C. The reaction mixture so formed is warmed to approximately 60° C. After a time period between about 1.5 hours to about 2.5 hours, preferably about 2 hours, the reaction mixture is once again cooled to a temperature approximately 0° C. and poured onto ice. The resulting sulfonyl chloride is then treated with gasseous or aqueous ammonia bubbled through a solution of the sulfonyl chloride in an aprotic solvent such as methylene chloride or ether.

In reaction 1 of Scheme 1, the isocyanate compound of formula X and the sulfonamide compound of formula IX are converted to the corresponding sulfonyl urea compound of formula VII by reacting IX and X in the presence of a base, such as sodium hydride, sodium hydroxide, triethylamine or 1,8-diazabicyclo[5,4,0]undec-7-ene, and a polar solvent, such as tetrahydrofuran, acetone or dimethylformamide. The reaction mixture so formed is heated to reflux for a time period between about 10 hours to about 14 hours, preferably about 12 hours.

Inhibition of ATP induced Release of IL-1B

Mononuclear cells are purified from 100 ml of blood isolated using LSM (Organon Teknika). The heparinized blood (1.5 ml of 1000 units/ml heparin for injectin from Apotheconis added to each 50 ml syringe) is diluted with 20 ml of Medium (RMI 1640, 5% FBS, 1% pen/strep, 25 mM HEPES, pH 7.3). 30 ml of the diluted blood is layered over 15 ml of LSM (Organon Teknika) in a 50 ml conical polypropylene centrifuge tube. The tubes are centrifuged at 1200 rpm for 30 minutes in benchtop Sorvall centrifuge at room temperature. The mononuclear cells, located at the interface of the plasma and LSM, are removed, diluted with Medium to achieve a final volume of 50 ml, and collected by centrifugation as above. The supernatant is discarded and the cell pellet is washed 2 times with 50 ml of medium. A 10 µl sample of the suspended cells is taken before the second wash for counting; based on this count the washed cells are diluted with medium to a final concentration of 2.0×106 cells/ml.

0.1 ml of the cell suspension is added to each well of 96 well plates. The monocytes are allowed to adhere for 2 hours, then non-adherent cells are removed by aspiration and the attached cells are washed twice with 100 µl f Medium. 100 µl of Medium is added to each well, and the cells are incubated, overnight at 37° C. in a 5% carbon dioxide incubator.

The following day, 25 µl of 50 ng/ml LPS (in Medium) is added to each well and the cells are activated for 2 hours at 37° C.

Test agents are diluted with dimethyl sulfoxide to a final concentration of 10 mM. From this stock solution compounds are first diluted to 1:50 [5 µl of 10 mM stock+245 µl Chase Medium (RPMI 1640, 25 mM Hepes, pH 6.9, 1% FBS, 1% pen/strep, 10 ng/ml LPS and 5 mM sodium bicarbonate]. A second dilution is prepared by adding 10 µl of the 200 µM test agent to 90 µl of Chase Medium yielding a final concentration of 20 µM test agent; the dimethyl sulfoxide concentration at this point is 0.2%.

The LPS-activated monocytes are washed once with 100 µl of Chase Medium then 100 µl of Chase Medium (containing 0.2% dimethyl sulfoxide) is added to each well. 0.011 ml of the 20 µM test agent solutions are added to the appropriate wells, and the monocytes are incubated for 30 minutes at 37° C. At this point 2 mM ATP is introduced by adding 12 µl of a 20 mM stock solution (previously adjusted to pH 7.2 with sodium hydroxide) and the cells are incubated for an additional 3 hours at 37° C.

The 96-well plates are centrifuged for 10 minutes at 2000 rpm in a Sorvall benchtop centrifuge to remove cells and cell debris. A 90 µl aliquot of each supernatant is removed and transferred to a 96 well round bottom plate and this plate is centrifuged a second time to ensure that all cell debris is removed. 30 µl of the resulting supernatant is added to a well of an IL-1β ELISA plate that also contains 70 µl of PBS, 1% FBS. The ELISA plate is incubated overnight at 4° C. The ELISA (R&D Systems) is run following the kit directions. Data Calculation and Analysis:

The amount of IL-1β immunoreactivity in the chase medium samples is calculated as follows:

% control=(X−B)/(TOT−B)×100 where X=OD450 nm of test compound well

B=OD450 of Reagent Blank wells on the ELISA

TOT=O.D450 of cells that were treated with 0.2% dimethyl sulfoxide only.

The compounds of the present invention can be administered in a wide variety of different dosage forms, in general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (intramuscular, intrapertioneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

The present invention is illustrated by the following examples, but it is not limited to the details thereof.

PREPARATION A

3-Tert-butylsulfamoyl-benzenesulfonyl chloride

A solution of 1.46 grams (20 mmole) of t-butylamine and 2.02 grams (20 mmole) of triethylamine in tetrahyrofuran was added dropwise to a solution of 5.5 grams (20 mmole) of 1,3-benzenesulfonyl chloride in tetrahydrofuran. The reaction was stirred at room temperature for 2 hours. The solvent was evaporated in vacuo. The residue was purified on silica gel eluting with methylene chloride to give 3.86 grams of the titled compound as an oil.

PREPARATION B

Benzene-1,3-disulfonic acid tert-butyl-amide methylamide 5 ml of a 33% solution of methylamine in ethanol was added to a solution of 1.8 grams (7 mmole) of 3-tert-butylsulfamoyl-benzenesulfonyl chloride in ethyl acetate. The mixture was stirred for 2 hours. The ethyl acetate layer was separated and concentrated in vacuo. The residue was purified on silica gel eluting 5% methanol in diochloromethane to give 1.32 grams of the titled compound as a white solid.

PREPARATION C

Benzene-1,3-disulfonic acid tert-butyl-amide dimethylamide

Dimethylamine gas was allowed to bubble for 3 minutes into a solution of 1.8 grams (7 mmole) of 3-tert-butylsulfamoyl-benzenesulfonyl chloride in ethyl acetate. Water was added and the mixture was stirred at room temperature for 1 hour. The ethyl acetate layer was separated, dried over magnesium sulfate and concentrated in vacuo to a solid which was triturated with hexane/isopropryl ether to give 1.59 grams of the titled compound, m.p. 100–102° C.

PREPARATION D

Benzene-1,3-disulfonic acid amide tert-butyl-amide 20 ml of concentrated ammonium hydroxide was added to a solution of 1 gram (3.2 mmole) 3-tert-butylsulfamoyl-benzenesulfonyl chloride in ethyl acetate. It was stirred vigorously for 8 hours. The ethyl acetate layer was separated dried over magnesium sulfate in vacuo to give 320 mg of the titled compound as a white solid. m.p. 151–154° C.

PREPARATION E

Benzene-1,3-disulfonic acid tert-butyl-amide cyclopropylamide

A mixture of 5 ml of cyclopropylamine and 10 ml of water was added to a solution of 1 gram (3.9 mmole) of 3-tert-butylsulfamoyl-benzenesulfonyl chloride in ethyl acetate. The mixture was stirred at room temperature for 2 hours. The ethyl acetate layer was separated, dried over magnesium sulfate and concentrated in vacuo to an oil which crystallized from isopropyl ether to give 839 mg of the titled compound as a solid.

PREPARATION F

Benzene-1,3-disulfonic acid tert-butyl-amide cyclobutylamide

Using a procedure similar to that described in Preparation E, 4 ml of cyclobutylamine was added to 1 gram (3.9 mmole) of 3-tert-butylsulfamoyl-benzenesulfonyl chloride to give 813 mg of the titled compound.

PREPARATION G

Benzene-1,3-disulfonic acid amide methylamide

A solution of 1.3 grams (4.3 mmole) of benzene-1,3-disulfonic acid tert-butylamidemethylamide in 15 ml of trifluroacetic acid containing 1 drop of anisole was stirred at room temperature for 12 hours. The trifluoroacetic acid was evaporated in vacuo and the residue triturated with methylene chloride to give 330 mg of the titled compound, m.p. 124–126° C.

The titled compounds of Preparations H–J were prepared by a method analogous to that described in Preparation D using the starting material indicated.

PREPARATION H

Benzene-1,3-disulfonic acid amide dimethylamide

Benzene-1,3-disulfonic acid tert-butyl-amide dimethylamide, m.p. 166–167° C.

PREPARATION I

Benzene-1,3-disulfonic acid amide cyclopropylamide

Benzene-1,3-disulfonic acid tert-butyl-amide cyclopropylamide, m.p. 120–121° C.

PREPARATION J

Benzene-1,3-disulfonic acid amide cyclobutylamide

Benzene-1,3-disulfonic acid tert-butyl-amide cyclobutylamide, m.p. 128–130° C.

PREPARATION K

3-Methylsulfanyl-benzenesulfonamide

A solution of 1.6M n-butyllithium (12.5 ml, 20 mmol) in hexane was added to a solution of m-bromothioanisole (4.06 grams, 20 mmol). The solution so formed was stirred at −78° C. for 3 hours. Sulfur dioxide was then bubbled into the reaction until it was acidic. The reaction was allowed to warm to room temperature overnight. A solution of N-chlorosuccinimide (2.4 grams, 78 mmol) in methylene chloride was added and after stirring for 1 hour at room temperature, the tetrahydrofuran was evaporated. The residue was slurried in methylene chloride and filtered. The filtrate was mixed with concentrated ammonium hydroxide and stirred at room temperature for 1 hour. The methylene chloride layer was dried and evaporated. The residue was triturated with methylene chloride to give 1.5 grams of the titled compound. mp:126–127° C.

PREPARATION L

3-Methylsulfinyl-benzenesulfonamide

A mixture of 3-methylsulfanyl-benzenesulfonamide (406 mg, 2 mmol) and N-chlorosuccinimide (268 mg, 2 mmol) in methanol was stirred at room temperature for 8 hours. The methanol was evaporated and the residue was slurried with methylene chloride and filtered. The filtrate was evaporated to give 250 mg of the titled compound as a white solid.

PREPARATION M

3-Methylsulfonyl-benzenesulfonamide

To a solution of 3-methylsulfanylbenzenesulfonamide (500 mg, 2.5 mmol) in acetone was added an aqueous solution of OXONE (3.2 grams, 5 mmol). The mixture was stirred at room temperature for 12 hours. The reaction was evaporated to dryness in vacuo. The residue was triturated with acetone and filtered. The filtrated was evaporated to give 460 mg of the titled compound.

PREPARATION N 1-(3-Bromo-phenyl)-cyclobutanol

To a solution of 1,3-dibromo-benzene (2.36 grams, 10 mmol) in tetrahydrofuran at −78° C. was added a 1.6M solution of n-butyllithium (6.3 ml, 10 mmol) in hexane and stirred for 4 hours. Cyclobutanone (700 mg, 10 mmol) was then added in one portion. After stirring for 2 hours at −78° C., the reaction was quenched with 2N hydrochloric acid. The reaction was warmed to room temperature, diluted with water and extracted with ethyl acetate. The ethyl acetate layer was dried and evaporated to give 2.5 grams of crude product which was purified on silica gel eluting with 50% methylene chloride in hexane to give 1.5 grams of the titled compound.

PREPARATION O 3-(1-Hydroxy-cyclobutyl)-benzenesulfonamide

A 1.6M solution of n-butyllithium (8 ml, 12.8 mmol) in hexane was added to a solution of 1-(3-bromo-phenyl)-cyclobutanol (1.44 grams, 6.4 mmol) in tetrahydrofuran at −78° C. After 30 minutes, at the reaction was allowed to warm to 0° C. Sulfur dioxide was bubbled into the reaction mixture and stirred for an additional 30 minutes. The tetrahydrofuran was evaporated and an aqueous solution of sodium acetate (4.1 grams, 50 mmol) and of hydroxylamine-sulfonic acid (1.85 grams, 16 mmol) was added. After stirring at room temperature for 2 hours, the reaction was acidified with 2N hydrochloric acid then extracted with ethyl acetate. The ethyl acetate was dried over sodium sulfate and evaporated. The residue was purified on silica gel with dichloromethane/ether to give 70 mg of the titled compound.

PREPARATION P 1-(3-Bromophenyl)-cyclopentanol

Using a procedure similar to that of Preparation N, from 2.36 grams of 1,3-dibromobenzene, 6.3 ml of 1.6M n-butyllithium and 840 mg of cyclopentanone, there was obtained 1.56 grams of 1-(3-bromophenyl)-cyclopentanol as an oil.

PREPARATION Q 3-(1-Hydroxy-cyclopentyl)-6-benzenesulfonamide

Using a procedure similar to that of Preparation O, from 1.5 grams of 1-(3-bromo-phenyl)-cylopentanol, 7.9 ml of 1.6M n-butyllithium, 1.85 grams of hydroxylamine-O-sulfonic acid and 4.1 grams of NaOAc, there was obtained 220 mg of 3-(1-hydroxy-cyclopentyl)-benzenesulfonamide as a white solid from dichloromethane. mp: 146–148° C.

PREPARATION R 1-(3-Bromophenyl)-cyclohexanol

Using a procedure similar to that of Preparation N, from 20 grams (85 mmoles) of 1,3-dibromobenzene, 53 ml of 1.6M n-butyllithium in hexane and 8.3 grams of cyclohexanone, there was obtained 4.9 grams of 1-(3-bromophenyl)-cyclohexanol as a white solid.

PREPARATION S 3-(1-hydroxy-cyclohexyl)benzenesulfonamide

A 1.6M solution of n-butyllithium (12.35 ml, 19.8 mmol) in hexane was added to a solution of 1-(3-bromophenyl)-cyclohexanol (2.4 grams, 9.4 mmol) in tetrahydrofuran at −78° C. The reaction was stirred for 1 hour, then sulfur dioxide was bubbled into the solution until it was acidic to wet pH paper. The reaction was allowed to warm to room temperature over 12 hours. N-chlorosuccinimide (1.38 grams, 10.3 mmole), dissolved in dichloromethane was added and the reaction stirred for 2 hours. The tetrahydrofuran was evaporated and the residue slurried with methylene chloride and filtered. The filtrate was evaporated to 2.1 grams of 3-(1-hydroxy-cyclohexyl)-benzenesulfonyl chloride as a brown oil. This was dissolved in methylene chloride and added dropwise to 20 ml of liquid ammonia. The ammonia was allowed to evaporated and the residue purified on silica gel with dichloromethane/methanol to give 250 mg of the title compound as a white solid.

The titled compounds of Preparations T–V were prepared by a method analogous to that described in Preparation K using the starting material indicated.

PREPARATION T 3-(2-Methyl-[1,3]dioxolan-2-yl)-benzenesulfonamide 2-(3-Bromophenyl)-2-methyl-[1,3]dioxolane. mp:96–98° C.

PREPARATION U

3-[1,3]Dioxolan-2-yl)-benzenesulfonamide 2-(3-Bromophenyl)-[1,3]dioxolane. mp:55–58° C.

PREPARATION V

2-Fluoro-5-(2-methyl-[1,3]dioxolan-2-yl)-benzenesulfonamide

2-[3-Bromo-4-fluorophenyl]-2-methyl-[1,3]dioxolane. mp:149–150° C.

PREPARATION W

[2-[4-bromo-2-nitro-phenyl)-vinyl]-dimethyl amine

A solution of 27 grams (0.125 mmoles) of 4-bromo-1-methyl-2-nitrobenzene and 1 ml (0.31 moles of N,N-dimethylformamide dimethyl acetal in 120 ml of DMF was heated at 80° C. for 2 hours. After cooling, the reaction was poured onto water and extracted with ethylacetate. Then was dried over sodium sulfate and evaporated to give 36 grams of the titled compound as a purple solid.

PREPARATION X

Acetic acid [2-(4-Bromo-2-nitro-phenyl)-ethyldiene-hydrazide

A solution of 36 grams of crude [2-[4-bromo-2-nitrophenyl)-vinyl]dimethylamine in 75 ml of dimethylformamide was cooled to 0° C. A solution of 26 grams of semicarbazide hydrochloride in 200 ml of water was added. 20 ml of concentrated hydrochloric acid was then added. The resulting solution was allowed to warm to room temperature. A tan precipitate was filtered, washed with water and dried.

PREPARATION Y

6-Bromo-1H-indole

A solution of 375 grams of iron (II) sulfate heptahydrate in 700 ml of water was added to a suspension of 35 grams of crude acetic acid [2-(4-bromo-2-nitrophenyl)-ethylidene-hydrazide 300 ml of concentrated ammonium hydroxide. The mechanically stirred mixture was heated to reflux for 4 hours, then cooled and filtered. The precipitate was triturated several times with hot ethyl acetate. The combined ethyl acetate layers were dried and evaporated to give 18 grams of the titled compound.

PREPARATION Z

1H-Indole-6-sulfonic acid amide

To a suspension of 3.5 (0.03 moles) of 35% KH in mineral oil in ether at 0° C. was added dropwise a solution of 6.0 grams 0.03 moles) of 6-bromo-1H-indole. After stirring for 1 hour, the light yellow solution was cooled to −78° C. 36.5 ml (0.06 moles) of a 1.7M solution of t-butyl lighium in pentane was added dropwise. After stirring for 1 hour at −78° C. $SO_2$ (g) was bubbled into the solution during 5 minutes. The reaction was allowed to warm to room temperature overnight. A solution of 4.1 grams (0.03 moles) of N-chlorosuccinimide was added in one portion. After stirring for 1 hour, the reaction was filtered to remove succinimide and the filtrate evaporated to a yellow solid. This was dissolved in tetrahydrofuran and added to 20 ml of liquid ammonia. The reaction was allowed to warm to room temperature. The residue was dissolved in ethyl acetate, washed with water, dried and evaporated to give 1.4 grams of the titled compound.

PREPARATION AA

5-Fluoro-2,3-dihydro-1H-indole

A solution of 6.8 grams (0.05 moles) of 5-fluoro-1H-indole in 50 ml of ether was cooled to 0° C. under nitrogen. 507 ml of a 0.15M solution of zinc borohydride in ether was added dropwise. The reaction was allowed to stir for 48 hours. The reaction was quenched with dilute hydrochloric acid. The pH was adjusted to 8.0 with dilute sodium hydroxide. The ether layer was separated, dried and evaporated to give 7 grams of the titled compound.

PREPARATION BB 1-(5-Fluoro-2,3-dihydro-indol-yl)-ethanone

Acetyl chloride (3 ml) was added dropwise to a solution of 7 grams of crude 5-fluoro-2,3-dihydro--1H-indole and 3 ml of triethylamine in 100 ml of $CH_2Cl_2$ at 0° C. After two hours, the reaction was diluted with water. The methylene chloride layer was separated, dried and evaporated to afford 7.3 grams of crude product which was purified on silica gel eluting with hexane/ethyl acetate to give 3.3 grams of the titled compound.

PREPARATION CC

1-Acetyl-5-fluoro-2,3-dihydro-1H-indole-6-sulfonic acid amide

Chlorosulfonic acid (35 ml) was cooled to 0° C. under nitrogen. 3 grams (0.016 moles of 1-(5-fluoro-2,3-dihydro-indol-yl)ethanone was added in portions. The reaction was heated a 50° for 3 hours, cooled and poured into ice. The resulting white precipitate was filtered off and dissolved in methylene chloride. A solution of concentrated ammonium hydroxide was added and the mixture stirred at room temperature for 1 hour. The volitiles were evaporated in vacuo and dilute hydrochloric acid was added. The precipitate was filtered and washed with water to give 3.6 grams of the titled compound.

PREPARATION DD

5-Fluoro-2,3-dihydro-1H-indole-6-sulfonic acid amide

A mixture of 3.6 grams of 1-Acetyl-5-fluoro-2,3-dihydro-1H-indole-6-sulfonic acid amide and 30 ml of 2N sodium hydroxide was heated at 100° C. for 3 hours. The reaction was cooled and the pH was adjusted to 7.0 with acetic acid. The resulting precipitate was filtered to give 3.0 grams of the titled compound.

PREPARATION EE

5-Fluoro-1H-indole-6-sulfonic acid amide

A mixture of 3 grams of mangenese dioxide and 3 grams of 5-fluoro-2,3-dihydro-1H-indole-6-sulfonic acid amide in 30 ml of dioxane was heated at 50° overnight. The reaction was filtered and the filtrate was evaporated to afford crude product which was purified on silica gel eluting with methylene chloride/ethyl acetate to give 1.1 grams of the titled compound. mp: 181–182° C.

PREPARATION FF 2-(3-Bromophenyl)propan-2-ol

To a stirred solution of methylmagnesium bromide (60 mL of a 3.0 M solution in diethyl ether) at 0° C. was added dropwise a solution of 3-bromoacetophenone (29.8 grams) in 75 mL of diethyl ether. Once the addition was complete, the mixture was stirred for 0.5 hours and poured into water. The aqueous phase was acidified with 1M hydrochloric acid and extracted with three portions of diethyl ether. The combined ether layers were washed with saturated sodium bicarbonate, concentrated to afford 30.4 grams of the title compound. $^1$H NMR δ7.72 (br s, 1), 7.49 (d, 1, J=7.8), 7.37 (d, 1, J=7.9), 7.25 (dd, 1, J=7.8, 7.9), 4.19 (s, 1), 1.50 (br s, 6).

PREPARATION GG 2-(3-Aminosulfonylphenyl)-propan-2-ol

To a stirred solution of 2-(3-bromophenyl)-propan-2-ol (30 grams) in tetrahydrofuran (1.5 L) at −78° C. was added methyllithium (110 mL of a 1.4 M solution in diethyl ether). The solution was stirred at −78° C. for 15 minutes, then butyllithium (61 mL of a 2.5 M solution in hexane) was added. The solution was stirred for 15 minutes at −78° C. at which point a slurry formed. To this slurry was added liquefied sulfur dioxide (approximately 5 equivalents) in one portion. The slurry was stirred at −78° C. for 5 minutes, then warmed to room temperature and stirred for an additional two hours. The mixture was concentrated in vacuo to afford a yellow solid which was taken up in water (418 mL). Sodium acetate (190 grams) and hydroxylamine O-sulfonic acid (47.3 grams) were added to the aqueous solution, and the solution was stirred overnight. The mixture was extracted with ethyl acetate and the organic phase was washed with brine, dried over anhydrous sodium sulfate and concentrated in vacuo. Purification by flash chromatography (2:1 ethyl acetate/hexane) gave 27 grams of the title compound, m.p. 107.2–108.2° C.

PREPARATION HH

4-Chloro-2,6-diisopropyaniline

To a stirred solution of 2,6-diisopropylaniline (47 grams) in N,N-dimethylformamide (886 mL) was added N-chlorosuccinimide (37.3 grams) and the mixture was stirred overnight. The resulting dark red solution was poured into water (12 L) and extracted with diethyl ether. The combined ether extracts were washed with water and brine, dried over anhydrous sodium sulfate and concentrated in vacuo. The resulting dark red oil was purified by filtration through silica gel, eluting with 6:1 hexane/methylene chloride to afford 32 grams of the title compound. $^1$H NMR δ 7.02 (s, 2), 3.71 (br s, 2), 2.91 (qq, 2, J=6.9 Hz), 1.27 (d, 6, J=6.9 Hz), 1.27 (d, 6, J=6.9 Hz).

PREPARATION II

4-Chloro-2,6-diisopropylphenylisocyanate

To a stirred solution of 4-chloro-2,6-diisoproplaniline (32 grams) and triethylamine (7.8 mL) in tetrahydrofuran (505 mL) was added triphosgene (14.9 grams). The mixture was refluxed for two hours with stirring. The tetrahyrofuran was then revolved in vacuo and the resulting oil was taken up in pentane and filtered through silica gel to afford 33.3 grams of the product. $^1$NMR δ 7.16 (s, 2), 3.22 (qq, 2, J=7.1 Hz), 1.25 (d, 6, J=7.1 Hz), 1.25 (d, 6, J=7.1 Hz).

PREPARATION JJ

2-[3-[[[(4-Chloro-2,6-diisopropylphenylamino)carbonyl]amino]sulfonyl]phenyl]propan-2-ol To a stirred solution of 2-(3-aminosulfonylphenyl)-propan-2-ol (26.5 grams) in tetrahyrofuran was added sodium hydride (5.2 grams of a 60% dispersion in mineral oil) in several portions. Once hydrogen evolution had subsided, 4-chloro-2,6-diisopropylphenylisocyanate (30.8 grams) was added in one portion, and the resulting mixture was heated to reflux for twelve hours. The mixture was then cooled to room temperature and concentrated in vacuo. The resulting foam was dissolved in water, made basic with 1N sodium hydroxide and extracted with two portions of 1:1 ether/hexane. The aqueous layer was acidified with 1N hydrochloric acid, and the resulting white solid was filtered, washed with water and dried. This afforded 50 grams of a white solid which was recrystallized from wet ethyl acetate/hexane afforded the title compound, melting point 160.5–162.0° C.

PREPARATION KK

5-Nitroisopthaloyl chloride

To a stirred solution of 5-nitroisopthalic acid (10 grams) in methylene chloride (943 mL) was added oxalyl chloride (12.3 mL) and N,N-dimethylformamide (1 drop). The reaction mixture was stirred at room temperature overnight. Removal of the solvent in vacuo afforded 10.63 grams of the title compound. $^1$H NMR δ 9.17 (s, 2), 9.07 (s, 1).

PREPARATION LL 3,5-Diacetylnitrobenzene

Magnesium turnings (2.27 grams) were stirred with ethanol (12 mL) and carbon tetrachloride (1 drop). Once hydrogen evolution was complete, diethyl malonate (15.18 grams) in diethyl ether (30 mL) was added and the mixture was refluxed until all of the magnesium was consumed. 5-Nitroisopthaloyl chloride (10 grams) in tetrahydrofuran (29 mL) was added to the mixture and reflux was continued for an additional 16 hours. The mixture was cooled in an ice bath and acidified with 10% sulfuric acid. The aqueous phase was extracted with ethyl acetate and the organic phase was concentrated in vacuo. The oily residue was taken up in acetic acid (72 mL) and water (14 mL) and sulfuric acid (4 mL) was added. The mixture was vigorously refluxed for 12 hours, then cooled in an ice bath. The mixture was neutralized with 3M sodium hydroxide and extracted with ethyl acetate. The organic phase was dried over sodium sulfate and concentrated in vacuo to afford 7.54 grams of the title compound. $^1$H NMR δ 8.90 (s, 2), 886 (s, 1), 2.78 (s, 6).

PREPARATION MM 3,5-Diacetylaniline

To a stirred solution of tin (II) chloride dihydrate (32.87 grams) in concentrated hydrochloric acid (93 mL) at 50° C. was added 3,5-diacethylnitrobenzene (7.54 grams). The heat was removed immediately and an exotherm occurred. The mixture was stirred for 5 minutes, cooled with an ice bath, and neutralized with saturated potassium carbonate solution. The aqueous phase was extracted with several portions of ethyl acetate, dried over anhydrous sodium sulfate and concentrated in vacuo to afford 3.01 grams of the title compound. $^1$H NMR δ 7.77 (s, 1), 7.48 (s, 2), 5.16 (br s, 2), 2.55 (s, 6).

PREPARATION NN 3,5-Diacetylbenzenesulfonamide

To a stirred solution of 3,5-diacetylaniline (3.00 grams) in a mixture of acetic acid (17 (mL) and hydrochloric acid (5.7 mL) was added a solution of sodium nitrate (1.27 grams) in 2.1 mL of water. The solution was stirred for 20 minutes. 14 mL of acetic acid was saturated with sulfur dioxide gas, and this mixture was added to the reaction, followed by cuprous chloride (0.63 grams). Significant foaming occurred. The reaction mixture was stirred for one hour, diluted with water, and extracted with three portions of ethyl acetate. The combined ethyl acetate extracts were washed with water, and concentrated. The resulting oil was taken up in diethyl ether, and ammonia gas was bubbled through the solution. The resulting slurry was filtered, and the solid was taken up in acetone and filtered to remove ammonium chloride. Removal of the acetone in vacuo afforded 1.48 grams of the title compound. m.p. 179.2–180.7° C.

PREPARATION OO

1-[3-[[[(4-Chloro-2,6-diisopropylphenylamino)carbonyl]amino]sulfonyl]-5-acetylphenyl]ethan-1-one The title compound was prepared as described in method A from 3,5-diacetylbenzenesulfonamide (0.35 grams). 4-chloro-2,6-diisopropylphenylisocyanate (0.37 grams), sodium hydride (0.06 grams of a 60% dispersion in mineral oil), in tetrahydrofuran (4 mL). This afforded 0.28 grams of the title compound, m.p. 201.9–203.4° C.

PREPARATION PP

3-Chloro-1-indan-5-yl-propan-1-one

To a stirred solution of indane (300 grams) and 3-chloropropionoyl chloride (323 grams) in methylene chloride (2 L) at 0° C. was added aluminum chloride (376 grams) over a period of 3 hours. Once the addition was complete, the cooling bath was removed and the mixture was warmed to room temperature and stirred until hydrogen chloride evolution ceased. The reaction was quenched by pouring onto a mixture of 3.5 kg of ice and 700 mL of concentrated hydrochloric acid. The layers were separated, and the aqueous phase was extracted with methylene chloride. The combined methylene chloride layers were washed with water, saturated sodium bicarbonate solution and brine. The organic phase was dried with anhydrous sodium sulfate and concentrated in vacuo. The residue was recrystallized from hexane to afford 282 grams of a yellow solid, m.p. 63.5–65.1° C.

PREPARATION QQ 3,5,6,7-Tetrahydro-2H-s-indacen-1-one

Concentrated sulfuric acid (550 mL) was added dropwise, with stirring over a time period of 2 hours to 137 grams of 3-chloro-1-indan-5-yl-propan-1-one. The resulting thick black solution was heated to 90° C. until hydrogen chloride evolution ceased (usually 1–4 hours). The mixture was then cooled to room temperature and poured onto 5 kg of ice. The resulting slurry was stirred overnight and filtered. The solid was washed with water until the water ran clear through the filter. The tan solid was then dried in vacuo and recrystallized from hexane to afford 90 grams of the title compound, m.p. 72.4–74.8° C.

PREPARATION RR 1,2,3,5,6,7-Hexahydro-s-indacene

A mixture of 3,5,6,7-tetrahydro-2H-s-indacen-1-one (90 grams), ethanol (1 L), 10% palladium on carbon (1–2 grams) and concentrated hydrochloric acid (50 mL) was hydrogenated on a Parr shaker at room temperature until hydrogen uptake ceased. The mixture was filtered through a Celite pad. The pad was washed with 1 L diethyl ether. The filtrate was diluted with water and the organic phase was separated. The aqueous phase was extracted with 1 L of ether, and the combined ether extracts were washed with water, saturated sodium bicarbonate solution and brine. The ether extracts were dried over anhydrous sodium sulfate and concentrated in vacuo. The resulting pale yellow solid was recrystallized from methanol to afford 61 grams of the title compound as colorless crystals, m.p. 56.6–58.5° C.

PREPARATION SS 1-(1,2,3,5,6,7-Hexahydro-s-indacen-4-yl)-ethanone

To a stirred solution of 1,2,3,5,6,7-Hexahydro-s-indacene (30 grams) and acetyl chloride (14.2 mL) in 120 mL of benzene at 0° C. was added 30 grams of aluminum chloride over a period of 1 hour. The cooling bath was removed and the solution was warmed to room temperature and stirred for 4 hours. The deep red mixture was then poured onto a mixture of 270 grams of ice and 50 mL of concentrated hydrochloric acid. The layers were separated and the aqueous phase was extracted with diethyl ether. The combined organic phases were washed with saturated sodium bicarbonate solution and brine, dried over anhydrous sodium sulfate and concentrated in vacuo to afford an orange solid which was recrystallized from hexane to give 34 grams of the title compound, m.p. 69.1–76.1° C.

PREPARATION TT 1-(1,2,3,5,6,7-Hexahydro-s-indacen-4-yl)-ethanone oxide

A mixture of 1-(1,2,3,5,6,7-Hexahydro-s-indacen-4-yl)-ethanone (33 grams), ethanol (250 mL) hydroxylamine hydrochloride (58.5 grams) and pyridine (80 mL) was heated to reflux for a period of 12 hours. The mixture was then cooled to room temperature and concentrated in vacuo. The residue was then treated with 500 mL of water and extracted with chloroform-methanol. The organic phase was dried over anhydrous sodium sulfate and concentrated in vacuo to afford 32 grams of the title compound as a mixture of E and Z isomers, 178.6–182.3° C.

PREPARATION UU

N-(1,2,3,5,6,7-Hexahydro-s-indacen-4-yl)-acetamide

A mixture of 1-(1,2,3,5,6,7-Hexahydro-s-indacen-4-yl)-ethanone oxime (85 grams) in 270 mL of trifluoroacetic acid was added dropwise to a stirred refluxing solution of 90 mL of trifluoroacetic acid over a period of ½ hour. The resulting purple solution was then refluxed for 1 hour. The solution was cooled to room temperature and the trifluoroacetic acid was removed in vacuo. The dark solid was triturated with ethyl acetate/hexanes to afford 83 grams of a grey solid which was used without further purification, m.p. 257.4–259.1° C.

PREPARATION VV 1,2,3,5,6,7-Hexahydro-s-indacen-4-ylamine

A slurry of N-(1,2,3,5,6,7-hexahydro-s-indacen-4yl)-acetamide (110 grams) in YY mL of 25% sulfuric acid was treated with enough ethanol to make a solution (ca YY mL). The resulting solution was heated to reflux for a period of 2 days. The resulting black solution was treated with charcoal at reflux, filtered hot and cooled to 0° C. The solution was then cautiously neutralized with 20% sodium hydroxide solution. The resulting slurry was then filtered and washed with water until the filtrate ran neutral. The tan solid was then isolated and dried in vacuo to give 80 grams of the title compound, m.p. 94.5–96.6° C., which was used without further purification. If necessary, the title compound can be recrystallized from methanol to afford a white solid.

PREPARATION WW 1,2,3,5,6,7-Hexahydro-s-indacene

To a stirred solution of 1,2,3,5,6,7-hexahydro-s-indacen-4-ylamine (77 grams) in tetrahydrofuran (1.5 L) and triethylamine (68.3 mL) was added triphosgene (43.9 grams) in one portion. The mixture was heated to reflux for ½ hour, then cooled to room temperature. The tetrahydrofuran was removed under reduced pressure, and the residue was taken up in pentane and filtered through a plug of silica gel. Removal of the pentane in vacuo afforded 80 grams of a white solid, m.p. 35.0–36.2° C.

PREPARATION XX 3-(1-Hydroxy-1-methyl)ethylfuran

To a stirred solution of 24.97 mL of methyl magnesium bromide (3M solution in diethyl ether) at 0° C. was added 4.82 mL of ethyl 3-furoate in diethyl ether. The mixture was heated gently using a warm water bath for 30 minutes. Upon completion, the mixture was poured into ice water, carefully acidified using a buffered solution, and extracted with diethyl ether. The ether extracts were combined, washed with brine, dried over sodium sulfate, and concentrated in vacuo. The tertiary alcohol furan was purified using flash column chromatography with 6:1 hexane/ethyl acetate. Recovery: 2.89 grams (64%). $^1$H NMR (400 MHz, Acetone-$d_6$) δ 1.45 (s, 3H), 1.46 (s, 3H), 3.89 (br s, 1H), 6.45 (br s, 1H), 7.41 (br s, 1H), 7.42 (br s, 1H).

PREPARATION YY

2-Aminosulfonyl-3-(1-hydroxy-1-methyl)ethylfuran

To a stirred mixture of 2.89 grams of tertiary alcohol furan in THF at −78° C. wa added 17.19 mL of methyl lithium (1.4M solution in diethyl ether) followed 5 minutes later by 18.51 mL of sec-butyl lithium (1.3M solution in cyclohexanes). The mixture continued to stir at −78° C. for 40 minutes and 5.02 mL of liquid $SO_2$ was added. The temperature was maintained at −78° C. for 5 minutes and was then warmed to room temperature with continued stirring for 2 hours. The THF was then removed in vacuo and the lithium sulfinate was dissolved in 76.4 mL of water followed by addition of 7.78 grams of hydroxylamine o-sulfonic acid and 31 grams of sodium acetate. This mixture stirred at room temperature overnight and was extracted with ethyl acetate. The ethyl acetate extracts were combined, washed with brine, dried over sodium sulfate, and concentrated in vacuo. The sulfonamide was purified using flash column chromatography with 2:1 hexane/ethyl acetate. Recovery: 1.91 grams (41%) m.p. 110.1–111.6° C.

PREPARATION ZZ 3-(1-Hydroxy-1-methyl)ethylthiophene

To a stirred solution of 3.17 mL of methyl magnesium bromide (3M solution in diethyl ether) at 0° C. was added 1 gram of 3-acetylthiophene in diethyl ether. The mixture was then allowed to stir for 30 minutes while warming to room temperature. Upon completion, the mixture was poured into ice water, acidified, and extracted with diethyl ether. The ether extracts were combined, washed with brine, dried over sodium sulfate, and concentrated in vacuo. Recovery: 800 mg (71%) $^1$H NMR (400 MHz, Acetone-$d_6$) δ 1.50 (s, 6H), 4.00 (br s, 1H), 7.15 (dd, 1H, J=1.4, 5), 7.23 (m, 1H), 7.33 (dd, 1H, J=3.1, 5).

PREPARATION AAA

2-Aminosulfonyl-3-(1-hydroxy-1-methyl)ethylthiophene

To a stirred mixture of 800 mg of tertiary alcohol thiophene in THF at 78° C. was added 4.22 mL of methyl-lithium (1.4M solution in diethyl ether) followed 5 minutes later by 4.55 mL of sec-butyl lithium (1.3M solution in cyclohexanes). The mixture continued to stir at −78° C. for 40 minutes and 1.23 mL of liquid $SO_2$ was added. The temperature was maintained at −78° C. for 5 minutes and was then warmed to room temperature with continued stirring for 2 hours. The THF was then removed in vacuo and the lithium sulfinate was dissolved in 19 mL of water followed by addition of 1.9 grams of hydroxylamine o-sulfonic acid and 7.66 grams of sodium acetate. This mixture stirred at room temperature overnight and as extracted with ethyl acetate. The ethyl acetate extracts were combined, washed with brine, dried over sodium sulfate, and concentrated in vacuo. The sulfonamide was purified using flash column chromatography with 2:1 hexane/ethyl acetate. Recovery: 600 mg (48%) m.p. 114.3–115.1° C.

EXAMPLE 1

1-(4-Chloro-2,6-diisopropyl-phenyl)-3-[3-(1-hydroxy-1-methylethyl)-benzenesulfonyl]-urea To a stirred solution of 2-(3-aminosulfonylphenyl)-propan-2-ol (26.5 grams) in tetrahydrofuran was added sodium hydride (5.2 grams of a 60% dispersion in mineral oil) in several portions. Once hydrogen evolution had subsided, 4-chloro-2,6-dissopropylphenylisocyanate (30.8 grams) was added in one portion, and the resulting mixture was heated to reflux for twelve hours. The mixture was then cooled to room temperature and concentrated in vacuo. The resulting foam was dissolved in water, made basic with 1N sodium hydroxide and extracted with two portions of a 1:1 ration of ether/hexane. The aqueous layer was acidified with 1N hydrochloric acid, and the resulting white solid was filtered, washed with water and dried. This afforded 50 grams of a white solid which was recrystallized from wet ethyl acetate/hexane afforded the title compound, melting point 160.5–162.0° C.

The titled compounds of Example 2–130 were prepared by a method analogous to that described in Example 1 using the reagents indicated.

EXAMPLE 2

1-(4-Chloro-2,6-diisopropyl-phenyl)-3-[3-(1-hydroxycyclopentyl)-benzenesulfonyl]-urea 3-1-Hydroxycyclopentyl-benzenesulfonamide; 4-Chloro-2,6-diisopropyl-phenyl isocyanate. mp: 155° C.

EXAMPLE 3

1-(4-Chloro-2,6-diisopropyl-phenyl)-3-[3-methylsulfamoyl-benzenesulfonyl]-urea

3-Methylsulfamoyl-benzenesulfonamide; 4-Chloro-2,6-diisopropyl-phenyl isocyanate. mp: 125–128° C.

EXAMPLE 4

1-(4-Chloro-2,6-diisopropyl-phenyl)-3-[3-dimethylsulfamoyl-benzenesulfonyl]-urea 3-Dimethylsulfamoyl-benzenesulfonamide; 4-Chloro-2,6-diisopropyl-phenyl isocyanate. mp: 101–106° C.

EXAMPLE 5

1-(4-Chloro-2,6-diisopropyl-phenyl)-3-[3-cyclopropylsulfamoyl-benzenesulfonyl]-urea 3-Cyclopropylsulfamoyl-benzenesulfonamide; 4-Chloro-2,6-diisopropyl-phenyl isocyanate. mp: 170–174° C.

EXAMPLE 6

1-(4-Chloro-2,6-diisopropyl-phenyl)-3-[3-cyclobutylsulfamoyl-benzenesulfonyl]-urea 3-Cyclobutylsulfamoyl-benzenesulfonamide; 4-Chloro-2,6-diisopropyl-phenyl isocyanate. mp: 140–143° C.

EXAMPLE 7

1-(4-Chloro-2,6-diisopropyl-phenyl)-3-[3-methylsulfanyl-benzenesulfonyl]-urea

3-Methylsulfanyl-benzenesulfonamide; 4-Chloro-2,6-diisopropyl-phenyl isocyanate. mp: 125–126° C.

EXAMPLE 8

1-(4-Chloro-2,6-diisopropyl-phenyl)-3-[3-methanesulfinyl-benzenesulfonyl]-urea

3-Methylsulfinyl-benzenesulfonamide; 4-Chloro-2,6-diisopropyl-phenyl isocyanate. mp: 226–227° C.

EXAMPLE 9

1-(4-Chloro-2,6-diisopropyl-phenyl)-3-[3-methanesulfonyl-benzenesulfonyl]-urea

3-Methylsulfonyl-benzenesulfonamide; 4-Chloro-2,6-diisopropyl-phenyl isocyanate. mp: ° C.

EXAMPLE 10

1-(4-Chloro-2,6-diisopropyl-phenyl)-3-[3-(1-hydroxycyclobutyl)-benzenesulfonyl]-urea 3-1-Hydroxycyclobutyl-benzenesulfonamide; 4-Chloro-2,6-diisopropyl-phenyl isocyanate. mp: 155–157° C.

EXAMPLE 11

1-(4-Chloro-2,6-diisopropyl-phenyl)-3-[3-(1-hydroxycyclopentyl)-benzenesulfonyl]-urea 3-1-Hydroxycyclopentyl-benzenesulfonamide; 4-Chloro-2,6-diisopropyl-phenyl isocyanate. mp: 155° C.

EXAMPLE 12

1-(4-Chloro-2,6-diisopropyl-phenyl)-3-[3-(1-hydroxycyclohexyl)-benzenesulfonyl]-urea 3-1-Hydroxycyclohexyl-benzenesulfonamide; 4-Chloro-2,6-diisopropyl-phenyl isocyanate. mp: 172–176° C.

EXAMPLE 13

1-(4-Chloro-2,6-diisopropyl-phenyl)-3-[3-(2-methyl-[1,3]dioxolan-2-yl)-benzenesulfonyl]-urea 3-(2-Methyl-[1,3dioxolan-2yl)-benzenesulfonamide; 4-Chloro-2,6-diisopropyl-phenyl isocyanate. mp: 155–157° C.

EXAMPLE 14

1-(4-Chloro-2,6-diisopropyl-phenyl)-3-(3-[1,3]dioxolan-2-yl)-benzenesulfonyl]-urea 3-([1,3Dioxolan-2yl)-benzenesulfonamide; 4-Chloro-2,6-diisopropyl-phenyl isocyanate. mp: 145–147° C.

EXAMPLE 15

1-(4-Chloro-2,6-diisopropyl-phenyl)-3-(2-fluoro-5-(2-methyl-[1,3]dioxolan-2-yl)-benzenesulfonyl]-urea 3-(2-Fluoro-5-(2-methyl-[1,3dioxolan-2yl)-benzenesulfonamide; 4-Chloro-2,6-diisopropyl-phenyl isocyanate. mp: 168–170° C. isocyanate. mp: 168–170° C.

EXAMPLE 16

1-[2-Fluoro-5-(2-methyl-(1,3)-dioxolan-2-yl)benzenesulfonyl]-3-(1,2,3,5,6,7-hexahydro-5-indacen-4-yl)urea

EXAMPLE 17

1-(4-Chloro-2,6-diisopropyl-phenyl)-3-[1H-indole-6-sulfonyl]-urea 3-(1H-indole-6-sulfonamide)-benzenesulfonamide; 4-Chloro-2,6-diisopropyl-phenyl isocyanate. mp: 220–221° C.

EXAMPLE 18

1-(1,2,3,5,6,7-Hexahydro-5-indacen-4-yl)-3-[1H-indole-6sulfonyl]-urea

EXAMPLE 19

1-(4-Chloro-2,6-diisopropyl-phenyl)-3-(5-fluoro-1H-indole-6-sulfonyl]-urea 3-(5-Fluoro-1H-indole-6-sulfonamide)-benzenesulfonamide; 4-Chloro-2,6-diisopropyl-phenyl isocyanate. mp: 226–227° C.

EXAMPLE 20

1-[5-Fluoro-1H-indole-6-sulfonyl]-3-(1,2,3,5,6,7-hexahydro-5-indacen-4-yl)urea

EXAMPLE 21

1-(4-Chloro-2,6-diisopropyl-phenyl)-3-[3-(1-hydroxyethyl)-5-trifluoromethyl-benzenesulfonyl]-urea 3-(1-Hydroxy-ethyl)-5-trifluoromethyl-benzenesulfonamide; 4-Chloro-2,6-diisopropyl-phenyl isocyanate. mp: 168.9–170.0° C.

EXAMPLE 22

1-(3-Acetyl-5-trifluoromethyl-benzensulfonyl)-3-(4-chloro-2,6-diisopropyl-phenyl)-urea 3-Acetyl-5-trifluoromethyl-benzenesulfonamide; 4-Chloro-2,6-diisopropyl-phenyl isocyanate. mp: 157.4–158.9° C.

EXAMPLE 23

1-(4-Chloro-2,6-diisopropyl-phenyl)-3-[3-(1-hydroxyethyl)-4-methyl-benzenesulfonyl]-urea 3-(1-Hydroxy-ethyl)-4-methyl-benzenesulfonamide; 4-Chloro-2,6-diisopropyl-phenyl isocyanate. mp: 155.2–158.2° C.

EXAMPLE 24

1-(3-Acetyl-4-methyl-benzensulfonyl)-3-(4-chloro-2,6-diisopropyl-phenyl)-urea

3-Acetyl-4-methyl-benzenesulfonamide; 4-Chloro-2,6-diisopropyl-phenyl isocyanate. mp: 152.5–154.6° C.

EXAMPLE 25

1-[3,5-Bis-(1-hydroxy-ethyl)-benzensulfonyl]-3-(4-chloro-2,6-diisopropyl-phenyl)-urea 3,5-Bis-(1-hydroxy-ethyl)-benzenesulfonamide; 4-Chloro-2,6-diisopropyl-phenyl isocyanate. mp: 175.3–176.8° C.

EXAMPLE 26

1-(4-Chloro-2,6-diisopropyl-phenyl)-3-[3-(1-hydroxyethyl)-5-iodo-benzenesulfonyl]-urea 3-(1-Hydroxy-ethyl)-5-iodo-benzenesulfonamide; 4-Chloro-2,6-diisopropyl-phenyl isocyanate. mp: 184.4–186.6° C.

EXAMPLE 27

1-(3-Acetyl-5-iodo-benzensulfonyl)-3-(4-chloro-2,6-diisopropyl-phenyl)-urea

3-Acetyl-5-iodo-benzenesulfonamide; 4-Chloro-2,6-diisopropyl-phenyl isocyanate. mp: 187.6–188.9° C.

EXAMPLE 28

1-(4-Chloro-2,6-diisopropyl-phenyl)-3-[4-fluoro-3-(1-hydroxy-ethyl)-benzenesulfonyl]-urea 4-Fluoro-3-(1-hydroxy-ethyl)-benzenesulfonamide; 4-Chloro-2,6-diisopropyl-phenyl isocyanate. mp: 149.7–151.8° C.

EXAMPLE 29

1-(3-Acetyl-4-fluoro-benzensulfonyl)-3-(4-chloro-2,6-diisopropyl-phenyl)-urea

3-Acetyl-4-fluoro-benzenesulfonamide; 4-Chloro-2,6-diisopropyl-phenyl isocyanate. mp: 171.8–173.4° C.

EXAMPLE 30

1-(4-Acetyl-thiophene-2-sulfonyl)-3-(4-chloro-2,6-diisopropyl-phenyl)-urea

4-Acetyl-thiophene-2-sulfonamide; 4-Chloro-2,6-diisopropyl-phenyl isocyanate. mp: 169.7–171.8° C.

EXAMPLE 31

1-(4-Chloro-2,6-diisopropyl-phenyl)-3-[4-(1-hydroxy-ethyl)-thiophene-2-sulfonyl]-urea 4-(1-Hydroxy-ethyl)-thiophene-2-sulfonamide; 4-Chloro-2,6-diisopropyl-phenyl isocyanate. mp: 164.5–166.6° C.

EXAMPLE 32

1-(4-Chloro-2,6-diisopropyl-phenyl)-3-[3-(2-hydroxyimino-propyl)-benzenesulfonyl]-urea 3-(2-Hydroxyimino-propyl)-benzenesulfonamide; 4-Chloro-2,6-diisopropyl-phenyl isocyanate. mp: 153.8–156.7° C.

EXAMPLE 33

1-(4-Chloro-2,6-diisopropyl-phenyl)-3-[3-(2-hydroxy-propyl)-benzenesulfonyl]-urea 3-(2-Hydroxy-propyl)-benzenesulfonamide; 4-Chloro-2,6-diisopropyl-phenyl isocyanate. mp: 148.7–149.9° C.

EXAMPLE 34

1-(4-Chloro-2,6-diisopropyl-phenyl)-3-[3-(2-oxo-propyl)-benzenesulfonyl]-urea 3-(2-Oxo-propyl)-benzenesulfonamide; 4-Chloro-2,6-diisopropyl-phenyl isocyanate. mp: 154.8–156.6° C.

EXAMPLE 35

1-(2,6-Diisopropyl-phenyl)-3-(3-propionyl-benzenesulfonyl)-urea

3-Propionyl-benzenesulfonamide; 2,6-Diisopropyl-phenylisocyanate. mp: 151.7–152.8° C.

EXAMPLE 36

1-(3-Acetyl-4-methyoxy-benzenesulfonyl)-3-(4-chloro-2,6-diisopropyl-phenyl)-urea 3-Acetyl-4-methoxy-benzenesulfonamide; 4-Chloro-2,6-diisopropyl-phenyl isocyanate. mp: 214.2–215.1° C.

EXAMPLE 37

1-(4-Chloro-2,6-diisopropyl-phenyl)-3-[3-(1-hydroxy-ethyl)-4-methoxy-benzenesulfonyl]-urea 3-(1-Hydroxy-ethyl)-4-methoxy-benzenesulfonamide; 4-Chloro-2,6-diisopropyl-phenyl isocyanate. mp: 164.9–166.1° C.

EXAMPLE 38

1-(4-Chloro-2,6-diisopropyl-phenyl)-3-[3-(1-hydroxy-propyl)-benzenesulfonyl]-urea 3-(1-Hydroxy-propyl)-benzenesulfonamide; 4-Chloro-2,6-diisopropyl-phenyl isocyanate. mp: 218.4–220.3° C.

EXAMPLE 39

1-(4-Chloro-2,6-diisopropyl-phenyl)-3-(3-propionyl-benzenesulfonyl)-urea

3-Propionyl-benzenesulfonamide; 4-Chloro-2,6-diisopropyl-phenyl isocyanate. mp: 149.1–152.2° C.

EXAMPLE 40

1-(4-Chloro-2,6-diisopropyl-phenyl)-3-[3-(1-hydroxy-ethyl)-benzenesulfonyl]-urea 3-(1-Hydroxy-ethyl)-benzenesulfonamide; 4-Chloro-2,6-diisopropyl-phenyl isocyanate. mp: 151.8–154.3° C.

EXAMPLE 41

1-(5-Acetyl-2-methoxy-benzensulfonyl)-3-(4-bromo-2,6-diisopropyl-phenyl)-urea

5-Acetyl-2-methoxy-benzenesulfonamide; 4-Bromo-2,6-diisopropyl-phenyl isocyanate. mp: 185.1–186.5° C.

EXAMPLE 42

1-(5-Acetyl-2-methoxy-benzensulfonyl)-3-(2,6-diisopropyl-phenyl)-urea

5-Acetyl-2-methoxy-benzenesulfonamide; 2,6-Diisopropyl-phenyl isocyanate. mp: 199.7–201.3° C.

EXAMPLE 43

1-(3-Acetyl-benzensulfonyl)-3-(4-chloro-2,6-diisopropyl-phenyl)-urea

3-Acetyl-benzenesulfonamide; 4-Chloro-2,6-diisopropyl-phenyl isocyanate. mp: 163.1–165.6° C.

EXAMPLE 44

1-(4-Chloro-2,6-diisopropyl-phenyl)-3-[3-(1-hydroxyimino-ethyl)-benzenesulfonyl]-urea 3-(1-Hydroxyimino-ethyl)-benzenesulfonamide; 4-Chloro-2,6-diisopropyl-phenyl isocyanate. mp: 158.4–160.0° C.

EXAMPLE 45

1-(4-Bromo-2,6-diisopropyl-phenyl)-3-(6-methyl-1,1-dioxo-1-thiochroman-7-sulfonyl)-urea 6-Methyl-1,1-dioxo-1-thiochroman-7-sulfonamide; 4-Bromo-2,6-diisopropyl-phenyl isocyanate. mp: 250.4–251.9° C.

EXAMPLE 46

1-(2,6-Diisopropyl-phenyl)-(6-methyl-1,1-dioxo-1-thiochroman-7-sulfonyl)-urea

6-Methyl-1,1-dioxo-1-thiochroman-7-sulfonamide; 2,6-Diisopropyl-phenyl isocyanate. mp: 242.7–245.2° C.

EXAMPLE 47

1-(2,6-Diisopropyl-phenyl)-3-[3-(1-hydroxy-ethyl)-benzenesulfonyl]-urea 3-(1-Hydroxy-ethyl)-benzenesulfonamide; 2,6-Diisopropyl-phenyl isocyanate. mp: 122.6–124.0° C.

EXAMPLE 48

1-(4-Bromo-2,6-diisopropyl-phenyl)-3-[3-(1-hydroxy-ethyl)-benzenesulfonyl]-urea 3-(1-Hydroxy-ethyl)-benzenesulfonamide; 4-Bromo-2,6-diisopropyl-phenyl isocyanate. mp: 142.5–144.8° C.

EXAMPLE 49

1-(3-Acetyl-benzensulfonyl)-3-(4-bromo-2,6-diisopropyl-phenyl)-urea

3-Acetyl-benzenesulfonamide; 4-Bromo-2,6-diisopropyl-phenyl isocyanate. mp: 231.4–233.6° C.

EXAMPLE 50

1-(3-Acetyl-4-hydroxy-benzensulfonyl)-3-(2,6-diisopropyl-phenyl)-urea

3-Acetyl-4-hydroxy-benzenesulfonamide; 2,6-Diisopropyl-phenylisocyanate. mp: 196.6–198.9° C.

EXAMPLE 51

1-(3-Acetyl-4-methoxy-benzensulfonyl)-3-(2,6-diisopropyl-phenyl)-urea

3-Acetyl-4-methoxy-benzenesulfonamide; 2,6-Diisopropyl-phenylisocyanate. mp: 203.4–205.7° C.

EXAMPLE 52

1-(3-Acetyl-benzensulfonyl)-3-(2-sec-butyl-6-ethyl-phenyl)-urea

3-Acetyl-benzenesulfonamide; 2-sec-Butyl-6-ethyl-phenylisocyanate. mp: 136.3–138.9° C.

EXAMPLE 53

1-(3-Acetyl-benzensulfonyl)-3-(2-isopropyl-6-methyl-phenyl)-urea

3-Acetyl-benzenesulfonamide; 2-isopropyl-6-methyl-phenyl isocyanate. mp: 136.8–138.9° C.

EXAMPLE 54

1-(3-Acetyl-benzensulfonyl)-3-(2-tert-butyl-6-methyl-phenyl)-urea

3-Acetyl-benzenesulfonamide; 2-tert-Butyl-6-methyl-phenyl isocyanate. mp: 155.4–157.7° C.

EXAMPLE 55

1-(3-Acetyl-benzensulfonyl)-3-(2-ethyl-6-isopropyl-phenyl)-urea

3-Acetyl-benzenesulfonamide; 2-Ethyl-6-isopropyl-phenyl isocyanate. mp: 127.1–128.5° C.

EXAMPLE 56

1-(3-Acetyl-benzensulfonyl)-3-(2,6-diisopropyl-phenyl)-urea

3-Acetyl-benzenesulfonamide; 2,6-Diisopropyl-phenyl isocyanate. mp: 151.6–153.5° C.

EXAMPLE 57

1-(4-Acetyl-2,6-diisopropyl-phenyl)-3-(3,5-diacetyl-benzenesulfonyl)-urea 3,5-Diacetyl-benzenesulfonamide; 4-Acetyl-2,6-diisopropyl-phenyl isocyanate. mp: 154.0–156.4° C.

EXAMPLE 58

4-[3-(3,5-Diacetyl-benzenesulfonyl)-ureido]-3,5-diisopropyl-benzamide 3,5-Diacetyl-benzenesulfonamide; 4-Isocyanato-3,5-diisopropyl-benzamide. mp: 198.5–199.8° C.

EXAMPLE 59

1-(4-Chloro-2,6-diisopropyl-phenyl)-3-[3-(2,2,2-trifluoro-1-hydroxy-ethyl)-benzenesulfonyl]-urea 3-(2,2,2-Trifluoro-1-hydroxy-ethyl)-benzenesulfonamide; 4-Chloro-2,6-diisopropyl-phenyl isocyanate. mp: 129.6–131.5° C.

EXAMPLE 60

1-(4-Chloro-2,6-diisopropyl-phenyl)-3-(3-trifluoroacetyl-benzenesulfonyl)-urea

3-Trifluoroacetyl-benzenesulfonamide; 4-Chloro-2,6-diisopropyl-phenyl isocyanate. mp: 88.4–89.1° C.

EXAMPLE 61

1-(4-Chloro-2,6-diisopropyl-phenyl)-3-[3-(1-hydroxy-2-methoxy-ethyl)-benzenesulfonyl]-urea 3-(1-Hydroxy-2-ethyl)-benzenesulfonamide; 4-Chloro-2,6-diisopropyl-phenyl isocyanate. mp: 108.7–109.2° C.

EXAMPLE 62

1-(4-Chloro-2,6-diisopropyl-phenyl)-3-(3-methoxyacetyl-benzenesulfonyl)-urea

3-Methoxyacetyl-benzenesulfonamide; 4-Chloro-2,6-diisopropyl-phenyl isocyanate. mp: 121.2–122.1° C.

EXAMPLE 63

4-[3-[3-(1-Hydroxy-ethyl)-benzenesulfonyl]-ureido]-3,5-diisopropyl-benzamide 3-(1-Hydroxy-ethyl)-benzenesulfonamide; 4-Isocyanato-3,5-diisopropyl-benzamide. mpL 204.6–205.9° C.

EXAMPLE 64

1-(4-Cyano-2,6-diisopropyl-phenyl)-3-[3-1-hydroxy-ethyl)-benzenesulfonyl]-urea 3-1-Hydroxy-ethyl)-benzenesulfonamide; 4-Cyano-2,6-diisopropyl-phenyl isocyanate. mp: 191.3–194.0° C.

EXAMPLE 65

1-(4-Chloro-2,6-diisopropyl-phenyl)-3-[3-1-hydroxy-2-methyl-propyl)-benzenesulfonyl]-urea 3-(1-Hydroxy-2-methyl-propyl)-benzenesulfonamide; 4-Chloro-2,6-diisopropyl-phenyl isocyanate. mp: 152.3–153.0° C.

EXAMPLE 66

1-(4-Chloro-2,6-diisopropyl-phenyl)-3-(3-isobutyryl-benzenesulfonyl)-urea

3-Isobutyryl-benzenesulfonamide; 4-Chloro-2,6-diisopropyl-phenyl isocyanate. mp: 170.2–171.4° C.

EXAMPLE 67

1-(2,6-Diisopropyl-4-thiophen-3-yl-phenyl)-3-[3-1-hydroxy-ethyl)-benzenesulfonyl]-urea 3-(1-Hydroxy-ethyl)-benzenesulfonamide; 2,6-Diisopropyl-4-thiophen-2yl-phenyl isocyanate. mp: 137.0–139.4° C.

EXAMPLE 68

1-(2,6-Diisopropyl-4-thiophen-2-yl-phenyl)-3-[3-1-hydroxy-ethyl)-benzenesulfonyl]-urea 3-(1-Hydroxy-ethyl)-benzenesulfonamide; 2,6-Diisopropyl-4-thiophen-2yl-phenyl isocyanate. mp: 98.4–99.9° C.

EXAMPLE 69

1-(3,5-Diisopropyl-biphenyl-4-yl)-3-[3-(1-hydroxy-ethyl)-benzensulfonyl]-urea 3-(1-Hydroxy-ethyl)-benzenesulfonamide; 4-Isocyanato-3,5-diisopropyl-biphenyl. mp: 127.4–128.6° C.

EXAMPLE 70

1-(4-Chloro-2,6-diisopropyl-phenyl)-3-(8-hydroxy-5,6,7,8-tetrahydro-naphthalene-2-sulfonyl)-urea 8-Hydroxy-5,6,7,8-tetrahydro-naphthalene-2-sulfonamide; 4-Chloro-2,6-diisopropyl-phenyl isocyanate. mp: 136.8–138.2° C.

EXAMPLE 71

1-(4-Chloro-2,6-diisopropyl-phenyl)-3-(8-oxo-5,6,7,8-tetrahydro-naphthalene-2-sulfonyl)-urea 8-Oxo-5,6,7,8-tetrahydro-naphthalene-2-sulfonamide; 4-Chloro-2,6-diisopropyl-phenyl isocyanate. mp: 180.0–182.4° C.

EXAMPLE 72

1-(4-Chloro-2,6-diisopropyl-phenyl)-3-(8-hydroxyimino-5,6,7,8-tetrahydro-naphthalene-2-sulfonyl)-urea 8-Hydroxyimino-5,6,7,8-tetrahydro-naphthalene-2-sulfonamide; 4-Chloro-2,6-diisopropyl-phenyl isocyanate. mp: 162.5–164.2° C.

EXAMPLE 73

1-(4-Bromo-2,6-diisopropyl-phenyl)-3-(8-hydroxy-5,6,7,8-tetrahydro-naphthalene-2-sulfonyl)-urea 8-Hydroxy-5,6,7,8-tetrahydro-naphthalene-2-sulfonamide; 4-Bromo-2,6-diisopropyl-phenyl isocyanate. mp: 164.0–165.8° C.

EXAMPLE 74

1-(2,6-Diisopropyl-phenyl)-3-(8-hydroxy-5,6,7,8-tetrahydro-naphthalene-2-sulfonyl)-urea 8-Hydroxy-5,6,7,8-tetrahydro-naphthalene-2-sulfonamide; 2,6-Diisopropyl-phenyl isocyanate. mp: 120.0–122.6° C.

EXAMPLE 75

1-(2,6-Diisopropyl-phenyl)-3-(8-hydroxyimino-5,6,7,8-tetrahydro-naphthalene-2-sulfonyl)-urea 8-Hydroxyimino-5,6,7,8-tetrahydro-naphthalene-2-sulfonamide; 2,6-Diisopropyl-phenyl isocyanate. mp: 139.2–140.0° C.

EXAMPLE 76

1-(4-Bromo-2,6-diisopropyl-phenyl)-3-(8-hydroxyimino-5,6,7,8-tetrahydro-naphthalene-2-sulfonyl)-urea 8-Hydroxyimino-5,6,7,8-tetrahydro-naphthalene-2-sulfonamide; 4-Bromo-2,6-diisopropyl-phenyl isocyanate. mp: 168.6–169.2° C.

EXAMPLE 77

1-(4-Bromo-2,6-diisopropyl-phenyl)-3-(8-oxo-5,6,7,8-tetrahydro-naphthalene-2-sulfonyl)-urea 8-Oxo-5,6,7,8-tetrahydro-naphthalene-2-sulfonamide; 4-Bromo-2,6-diisopropyl-phenyl isocyanate. mp: 208.0–208.8° C.

EXAMPLE 78

1-(2,6-Diisopropyl-phenyl)-3-(8-oxo-5,6,7,8-tetrahydro-naphthalene-2-sulfonyl)-urea 8-Oxo-5,6,7,8-tetrahydro-naphthalene-2-sulfonamide; 2,6-Diisopropyl-phenyl isocyanate. mp: 197.4–198.0° C.

EXAMPLE 79

3-[3-(4-Bromo-2,6-diisopropyl-phenyl)-ureidosulfonyl]-benzamide

3-Sulfonamido-benzamide; 4-Bromo-2,6-diisopropyl-phenyl isocyanate. mp: 180.0–180.6° C.

EXAMPLE 80

1-(4-Chloro-2,6-diisopropyl-phenyl)-3-[3-(1,2-dihydroxy-ethyl)-benzenesulfonyl]-urea 3-(1,2-Dihydroxy-ethyl)-benzenesulfonamide; 4-Chloro-2,6-diisopropyl-phenyl isocyanate. mp: 169.7–171.2° C.

EXAMPLE 81

3-[3-(2,6-Diisopropyl-phenyl)-ureidosulfonyl]-benzamide

3-Sulfonamido-benzamide; 2,6-Diisopropyl-phenyl isocyanate. mp: 182.3–184.1° C.

EXAMPLE 82

3-[3-(4-Bromo-2,6-diisopropyl-phenyl)-ureidosulfonyl]-N-methyl-benzamide

3-Sulfonamido-N-methyl-benzamide; 4-Bromo-2,6-diisopropyl-phenylsocyanate. mp: 243.8–245.1° C.

EXAMPLE 83

3-[3-(2,6-Diisopropyl-phenyl)-ureidosulfonyl]-N-methyl-benzamide

3-Sulfonamido-N-methyl-benzamide; 2,6-Diisopropyl-phenyl isocyanate. mp: 236.2–237.2° C.

EXAMPLE 84

1-(5-Acetyl-2-bromo-benzenesulfonyl)-3-(4-bromo-2,6-diisopropyl-phenyl)-urea

5-Acetyl-2-bromo-benzenesulfonamide; 4-Bromo-2,6-diisopropyl-phenyl isocyanate. mp: 177.2–179.1° C.

EXAMPLE 85

1-[2-Chloro-5-(1-hydroxy-ethyl)-benzenesulfonyl]-3-(2,6-diisopropyl-phenyl)-urea 2-Chloro-5-(1-hydroxy-ethyl)-benzenesulfonamide; 2,6-Diisopropyl-phenyl isocyanate. mp: 154.0–156.0° C.

EXAMPLE 86

1-[2-Chloro-5-(1-hydroxy-ethyl)-benzenesulfonyl]-3-(4-bromo-2,6-diisopropyl-phenyl)-urea 2-Chloro-5-(1-hydroxy-ethyl)-benzenesulfonamide; 4-Bromo-2,6-diisopropyl-phenyl isocyanate. mp: 144.3–146.2° C.

EXAMPLE 87

1-[2-Chloro-5-(1-hydroxyimino-ethyl)-benzenesulfonyl]-3-(2,6-diisopropyl-phenyl)-urea 2-Chloro-5-(1-hydroxyimino-ethyl)-benzenesulfonamide; 2,6-Diisopropyl-phenyl isocyanate. mp: 156.6–158.0° C.

EXAMPLE 88

1-[2-Chloro-5-(1-hydroxyimino-ethyl)-benzenesulfonyl]-3-(4-bromo-2,6-diisopropyl-phenyl)-urea 2-Chloro-5-(1-hydroxyimino-ethyl)-benzenesulfonamide; 4-Bromo-2,6-diisopropyl-phenyl isocyanate. mp: 185.0–186.2° C.

EXAMPLE 89

1-(5-Acetyl-2-chloro-benzenesulfonyl)-3-(2,6-diisopropyl-phenyl)-urea

5-Acetyl-2-chloro-benzenesulfonamide; 2,6-Diisopropyl-phenyl isocyanate. mp 180.7–182.3° C.

EXAMPLE 90

1-(5-Acetyl-2-chloro-benzenesulfonyl)-3-(4-bromo-2,6-diisopropyl-phenyl)-urea

5-Acetyl-2-chloro-benzenesulfonamide; 4-Bromo-2,6-diisopropyl-phenyl isocyanate. mp: 175.2–176.5° C.

EXAMPLE 91

3-[3-(2,6-Diisopropyl-phenyl)-ureidosulfonyl]-N,N-dimethyl-benzamide

3-Sulfonamido-N,N-dimethyl-benzamide; 2,6-Diisopropyl-phenyl isocyanate. mp 211.8–212.6° C.

EXAMPLE 92

3-[3-(4-Bromo-2,6-diisopropyl-phenyl)-ureidosulfonyl]-N,N-dimethyl-benzamide

3-Sulfonamido-N,N-dimethyl-benzamide; 4-Bromo-2,6-diisopropyl-phenyl isocyanate. mp 225.7–227.6° C.

EXAMPLE 93

1-(2,6-Diisopropyl-phenyl)-3-(3-formyl-benzenesulfonyl)-urea

3-Formyl-benzenesulfonamide; 2,6-Diisopropyl-phenyl isocyanate. mp: 108.3–109.0° C.

EXAMPLE 94

1-(2,6-Diisopropyl(hydroxyimino-methyl)-benzenesulfonyl]-urea 3-(Hydroxyimino-methyl)-benzenesulfonamide; 2,6-Diisopropyl-phenyl isocyanate. mp: 107.0–108.1° C.

EXAMPLE 95

1-(2,6-Diisopropyl-phenyl)-3-[3-(1-methoxyimino-ethyl)-benzenesulfonyl]-urea 3-(1-Methoxyimino-ethyl)-benzenesulfonamide; 2,6-Diisopropyl-phenyl isocyanate. mp: 164.9–165.9° C.

EXAMPLE 96

1-[3-(1-Benzyloxyimino-ethyl)-benzenesulfonyl]-3-(2,6-diisopropyl-phenyl)-urea 3-(1-Benzyloxyimino-ethyl)-benzenesulfonamide; 2,6-Diisopropyl-phenyl isocyanate. mp: 136.5–139.0° C.

EXAMPLE 97

1-(2,6-Diisopropyl-phenyl)-3-[3-(1-ethoxyimino-ethyl)-benzenesulfonyl]-urea 3-(1-Ethoxyimino-ethyl)-benzenesulfonamide; 2,6-Diisopropyl-phenylisocyanate. mp: 156.9–158.4° C.

EXAMPLE 98

1-{3-[3-(2,6-Diisopropyl-phenyl)-ureidosulfonyl]-phenyl}-ethylideneaminooxy)-acetic acid 3-Sulfonamido-phenyl-(1-ethylideneaminooxy)-acetic acid; 2,6-Diisopropyl-phenyl isocyanate. mp: 107.1–107.7° C.

EXAMPLE 99

1-(2,6-Diisopropyl-phenyl)-3-[3(1-hydroxyimino-ethyl)-benzenesulfonyl]-urea

3(1-Hydroxyimino-ethyl)-benzenesulfonamide; 2,6-Diisopropyl-phenyl isocyanate. mp: 131.0–132.6° C.

EXAMPLE 100

1-(2,6-Diisopropyl-phenyl)-3(3-methanesulfonyl-benzenesulfonyl)-urea

3-Methanesulfonyl-benzenesulfonamide;2,6-Diisopropyl-phenylisocyanate.mp: 99.5–100.6° C.

EXAMPLE 101

1-(2,6-Diisopropyl-phenyl)-3(3-methanesulfinyl-benzenesulfonyl)-urea

3-Methanesulfinyl-benzenesulfonamide; 2,6-Diisopropyl-phenyl isocyanate. mp: 217.4–221.0° C.

EXAMPLES 102

3-[3-(2,6-Diisopropyl-phenyl)ureidosulfonyl]-benzenesulfonamide

3-Sulfonamido-benzenesulfonamide; 2,6-Diisopropyl-phenyl isocyanate. mp: 131.4–133.5° C.

EXAMPLE 103

1-(4-Bromo-2,6-diisopropyl-phenyl)-3-(3-formyl-benzenesulfonyl)-urea 3-Formyl-benzenesulfonamide;4-Bromo-2,6-diisopropyl-phenylisocyanate.mp: 127.2–128.6° C.

EXAMPLE 104

1-[3-(2-Acetyl-phenoxymethyl)-benzenesulfonyl]-3(2,6-diisopropyl-phenyl)-urea 3-(2-Acetyl-phenoxymethyl)-benzenesulfonamide; 2,6Diisopropyl-phenyl isocyanate. mp: 124.2–125° C.

EXAMPLE 105

1-[3-(1-Amino-ethyl)-benzenesulfonyl]-3(2,6-diisopropyl-phenyl)-urea hydrochloride 3-(1-Amino-ethyl)-benzenesulfonamide hydrochloride; 2,6-Diisopropyl-phenyl isocyanate. mp:210.6–212.9° C.

EXAMPLE 106

1-(2,6-Diisopropyl-phenyl)-3-(3-furan-2-yl-benzenesulfonyl)-urea

3-Furan-2-yl-benzenesulfonamide; 2,6-Diisopropyl-phenyl isocyanate. mp: 196.6–198.0° C.

EXAMPLE 107

1-(2,6-Diisopropyl-phenyl)-3-(4-furan-2-yl-benzenesulfonyl)-urea

4-Furan-2-yl-benzenesulfonamide; 2,6-Diisopropyl-phenyl isocyanate. mp: 201.5–202.7° C.

EXAMPLE 108

1-(1,2,3,5,6,7-Hexahydro-s-indacen-4-yl)-3-[4-(1-Hydroxyimino-ethyl)-thiophene-2-sulfonyl]-urea 4-(1-Hydroxyimino-ethyl)-thiophene-2-sulfonamide; 4Isocyanato-1,2,3,5,6,7-hexahydro-s-indacene. mp:261.8–266.1° C.

EXAMPLE 109

1-(4-Acetyl-thiophene-2-sulfonyl)-3-(1,2,3,5,6,7-hexahydro-s-indacen-4-yl)-urea

4-Acetyl-thiophene-2-sulfonamide; 4-lsocyanato-1,2,3,5, 6,7-hexahydro-s-indacene. mp: 270.2–272.3° C.

EXAMPLE 110

1-(1,2,3,5,6,7-Hexahydro-s-indacen-4-yl)-3-[5-(1-hydroxy-1-methyl-ethyl)-thiophene-3-sulfonyl]-urea 5-(1-Hydroxy-1-methyl-ethyl)-thiophene-3-sulfonamide4-Isocyanato-1,2,3,5,6,7-hexahydro-s-indacene. mp:149.5–154.8° C.

EXAMPLE 111

1-(2,6-Diisopropyl-phenyl)-3-[4-(1-hydroxy-1-methyl-ethyl)-thiophene-2-sulfonyl]-urea 4-(1-Hydroxy-1-methyl-ethyl)-thiophene-2-sulfonamide; 2,6-Diisopropyl-phenyl isocyanate. mp=124.6–127.4° C.

EXAMPLE 112

1-(2,6-Diisopropyl-phenyl)-3-[4-(1-hydroxy-1-methyl-ethyl)-furan-2-sulfonyl]-urea 4-(1-Hydroxy-1-methyl-ethyl)-furan-2-sulfonamide; 2,6-Diisopropyl-phenyl isocyanate. mp:121.3–126.4° C.

EXAMPLE 113

1-(1,2,3,5,6,7-Hexahydro-s-indacen-4-yl)-3-[4-(1-hydroxy-1-methyl-ethyl)-thiophene-2-sulfonyl]-urea 4-(1-Hydroxy-1-methyl-ethyl)-thiophene-2-sulfonamide4-Isocyanato-1,2,3,5,6,7-hexahydro-s-indacene. mp:133.1–134.0° C.

EXAMPLE 114

1-(1,2,3,5,6,7-Hexahydro-s-indacen-4-yl)-3-[4-(1-hydroxy-1-methyl-ethyl)-furan-2-sulfonyl]-urea 4-(1-Hydroxy-1-methyl-ethyl)-furan-2-sulfonamide; 4-Ilsocyanato-1,2,3,5,6,7-hexahydro-s-indacene. mp: 153.8–154.4° C.

EXAMPLE 115

1-(8-Chloro,1,2,3,5,6,7-hexahydro-s-indacen-4-yl)-3-[4-(1-hydroxy-1-methyl-ethyl)-furan-2-sulfonyl]-urea 4-(1-Hydroxy-1-methyl-ethyl)-furan-2-sulfonamide; 4-Chloro-8-isocyanato-1,2,3,5,6,7-hexahydro-s-indacene. mp:163.7° C. (decomposed).

EXAMPLE 116

1-(4-Formyl-furan-2-sulfonyl)-3-(1,2,3,5,6,7-hexahydro-s-indacen-4-yl)-urea

4-Formyl-furan-2-sulfonamide; 4-isocyanato-1,2,3,5,6,7-hexahydro-s-indacene. mp: 281.3–284.1° C.

EXAMPLE 117

1-(1,2,3,5,6,7-Hexahydro-s-indacen-4-yl)-3-(4-hydroxymethyl-thiophene-2-sulfonyl)-urea 4-Hydroxymethyl-thiophene-2-sulfonamide; 4-Isocyanato-1,2,3,5,6,7-hexahydro-s-indacene. mp:273.9–275.8° C.

EXAMPLE 118

1-(4-Formyl-thiophene-2-sulfonyl)-3-(1,2,3,5,6,7-hexahydro-s-indacen-4yl)-urea

4-Formyl-thiophene-2-sulfonamide; 4-Isocyanato-1,2,3, 5,6,7-hexahydro-s-indacene. mp: 146.3–148.9° C.

EXAMPLE 119

1-(4-Chloro-2.6-diisopropyl-phenyl)-3-[4-(1-hydroxyimino-ethyl)-thiophene-2-sulfonyl]-urea 4-(1-Hydroxyimino-ethyl)-thiophene-2-sulfonamide; 4-Chloro-2,6-diisopropyl-phenyl isocyanate. mp:184.7–187.8° C.

EXAMPLE 120

1-(4-Chloro-2,6-diisopropyl-phenyl)-3-[5-(1-hydroxy-1-methyl-ethyl)-furan-2-sulfonyl]-urea 5-(1-Hydroxy-1-methyl-ethyl)-furan-2-sulfonamide; 4-Chloro-2,6-diisopropyl-phenyl isocyanate. mp: 116.0–117.9° C.

EXAMPLE 121

1-(4-Chloro-2,6-diisopropyl-phenyl)-3-[4-(1-hydroxy-1methyl-ethyl)-furan-2-sulfonyl]-urea 4-(1-Hydroxy-1-methyl-ethyl)-furan-2-sulfonamide; 4-Chloro-2,6-diisopropyl-phenyl isocyanate. mp: 127.4–129.2° C.

EXAMPLE 122

1-(4-Chloro-2,6-diisopropyl-phenyl)-3-[4-(1-hydroxy-1methyl-ethyl)-thiophene-2-sulfonyl]-urea 4-(1-Hydroxy-1-methyl-ethyl)-thiophene-2-sulfonamide4-Chloro-2,6-diisopropyl-phenyl isocyanate. mp: 131.2–133.6° C.

EXAMPLE 123

1-(4-Chloro-2,6-diisopropyl-phenyl)-3-[5-(1-hydroxy-1methyl-ethyl)-thiophene-2-sulfonyl]-urea sodium salt 5-(1-Hydroxy-1-methyl-ethyl)-thiophene-2-sulfonamide4-Chloro-2,6-diisopropyl-phenyl isocyanate. mp: 270.3–271.9° C.

EXAMPLE 124

1-(4-[1,3]Dioxolan-2-yl-thiophene-2-sulfonyl)-3-(1,2,3, 5,6,7-hexahydro-s-indacen-4-yl)-urea 4-[1,3]Dioxolan-2-yl-thiophene-2-sulfonamide; 4-Isocyanato-1,2,3,5,6,7-hexahydro-s-indacene. mp:224.7–226.6° C.

EXAMPLE 125

1-(4-[1,3]Dioxolan-2-yl-furan-2-sulfonyl)-3-(1,2,3,5,6,7-hexahydro-s-indacen-4-yl)-urea 4-[1,3]Dioxolan-2-yl-furan-2-sulfonamide; 4-Isocyanato-1,2,3,5,6,7-hexahydro-s-indacene. mp:183.5° C. (decomposition).

EXAMPLE 126

1-[3-(4,5-Dihydro-1H-imidazol-2-yl)-benzenesulfonyl]-3-(1,2,3,5,6,7-hexahydro-s-indacen-4-yl)-urea 3-(4,5Dihydro-1H-imidazol-2-yl)-benzenesulfonamide;4-Isocyanato-1,2,3,5,6,7-hexahydro-s-indacene. mp:241.0° C. (decomposition).

EXAMPLE 127

1-(1H-Benzoimidazole-5sulfonyl)-3-(1,2,3,5,6,7-hexahydro-s-indacen-4-yl)-urea

1H-Benzoimidazole-5-sulfonamide; 4-Isocyanato-1,2,3, 5,6,7-hexahydro-s-indacene. mp:239.0° C. (decomposition).

EXAMPLE 128

1-(1,2,3,5,6,7-Hexahydro-s-indacen-4-yl)-3-[3-(1-hydroxyimino-ethyl)-benzensulfonyl]-urea 3-(1-Hydroxyimino-ethyl)-benzenesulfonamide; 4-Isocyanato-1,2,3,5,6,7-hexahydro-s-indacene. mp:249.8° C. (decomposition).

EXAMPLE 129

1-(4-Chloro-2,6-diisopropyl-phenyl)-3-[3-tert-butylsulfamoyl-benzenesulfonyl]urea Benzene-1,3-disulfonic acid amide ter-butyl-amide; 5-Chloro-2-isocyanto-1,3-diisopropyl-benzene.

EXAMPLE 130

1-(4-Chloro-2,6-diisopropyl-phenyl)-3-[3-sulfamoyl-benzenesulfonyl]-urea

Using a procedure similar to that of preparation G, from 200 mg (0.38 mmole) of 1-(4-chloro-2,6-diisopropyl-phenyl)-3-[3-tert-butylsulfamoyl-benezenesulfonyl]-urea, there was obtained 92 mg of the titled compound as a white solid. mp: 172–177° C.

What is claimed is:

1. A compound of the formula

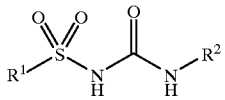

I or a pharmaceutically acceptable salt thereof, wherein
R$^1$ is a group of the formula

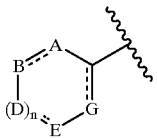

II wherein the broken lines represent optional double bond;
n is 0, 1, 2 or 3;
A, B, D, E and G are each independently oxygen, sulfur, nitrogen or Cr$^5$R$^6$ wherein R$^5$ and R$^6$ are each independently selected from hydrogen, (C$_1$–C$_6$)alkyl optionally substituted by one or two groups selected from C$_1$–C$_6$alkylamino, (C$_{1C6}$)alkylthio, (C$_{1-C6}$) alkoxy, hydroxy, cyano, perfluoro(C$_1$–C$_6$)alkyl, (C$_6$–C$_{10}$)aryl, (C$_5$–C$_9$)heteroaryl, (C$_6$–C$_{10}$)arylamino, (C$_6$–C$_{10}$)arylthio, (C$_6$–C$_{10}$)aryloxy wherein the aryl group is optionally substituted by (C$_1$–C$_6$)alkoxy, (C$_{1-C6}$)acyl, carboxy, hydroxy or halo; (C$_5$–C$_9$) heteroarylamino, (C$_5$–C$_9$)heteroarylthio, (C$_5$–C$_9$) heteroaryloxy, (C$_6$–C$_{10}$)aryl(C$_{6-C10}$)aryl, (C$_3$–C$_6$) cycloalkyl, hydroxy, piperazinyl, (C$_6$–C$_{10}$)aryl(C$_1$–C$_6$) alkoxy, (C$_5$–C$_9$)heteroaryl(C$_1$–C$_6$)alkoxy, (C$_1$–C$_6$) acylamino, (C$_1$–C$_6$)acylthio, (C$_1$–C$_{C6}$), acyloxy, (C$_1$–C$_6$)alkylsulfinyl, (C$_6$–C$_{10}$)arylsulfinyl, (C$_1$–C$_6$) alkylsulfonyl, (C$_6$–C$_{10}$)arylsulfonyl, amino, (C$_1$–C$_6$) alkylamino or ((C$_1$–C$_6$)alkyl)$_2$amino; halo, cyano, amino, hydroxy, perfluoro(C$_1$–C$_6$)alkyl, perfluoro (C$_1$–C$_6$)alkoxy, (C$_2$–C$_6$)alkenyl, carboxy(C$_2$–C$_6$) alkenyl, (C$_2$–C$_6$)alkynyl, (C$_1$–C$_6$)alkylamino, ((C$_1$–C$_6$) alkyl)$_2$amino, (C$_1$–C$_6$)alkylsulfonylamido, (C$_1$–C$_6$) alkylsulfinyl, aminosulfonyl, (C$_1$–C$_6$) alkylaminosulfonyl, ((C$_1$–C$_6$)alkyl)$_2$aminosulfonyl, (C$_1$–C$_6$)alkylthio, (C$_1$C$_6$)alkoxy, perfluoro(C$_1$–C$_6$) alkyl, (C$_6$–C$_{10}$)aryl, (C$_5$–C$_9$)heteroaryl, (C$_6$–C$_{10}$) arylamino, (C$_6$–C$_{10}$)arylthio, (C$_6$–C$_{10}$)aryl(C$_1$–C$_6$) alkoxy, (C$_5$–C$_9$)heteroarylamino, (C$_5$–C$_9$) heteroarylthio, (C$_5$–C$_9$)heteroaryloxy, (C$_3$–C$_6$) cycloalkyl, (C$_1$–C$_6$)acylamino, (C$_1$–C$_6$)acylthio, (C$_1$–C$_6$)acyloxy, R$^7$(C$_1$–C$_6$)alkyl wherein R$^7$ is (C$_1$–C$_6$)acylpiperazino, (C$_6$–C$_{10}$)arylpiperazino, (C$_5$–C$_9$)heteroarylpiperazino, (C$_1$–C$_6$)alkylpiperazino, (C$_6$–C$_{10}$)aryl(C$_1$–C$_6$)alkylpiperazino, (C$_5$–C$_9$) heteroaryl(C$_1$–C$_6$)alkylpiperazino, morpholino, thiomorpholino, piperidino, pyrrolidino, piperidyl, (C$_1$–C$_6$)alkylpiperidyl, (C$_6$–C$_{10}$)arylpiperidyl, (C$_5$–C$_9$) heteroarylpiperidyl, (C$_1$–C$_6$)alkylpiperidyl(C$_1$–C$_6$) alkyl,(C$_6$–C$_{10}$)arylpiperidyl(C$_1$–C$_6$)alkyl, (C$_5$–C$_9$) heteroarylpiperidyl(C$_1$–C$_6$)alkyl or (C$_1$–C$_6$) acylpiperidyl;

or a group of the formula

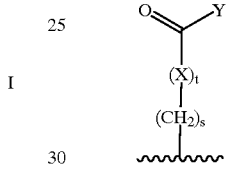

III wherein s is 0 to 6;
t is 0 or 1;
X is oxygen or NR$^8$ wherein R$^8$ is hydrogen, (C$_1$–C$_6$)alkyl or (C$_3$–C$_7$)cycloalkyl(C$_1$–C$_6$)alkyl;
Y is hydrogen, hydroxy, (C$_1$–C$_6$)alkyl, optionally substituted by halo, hydroxy or cyano; (C$_1$–C$_6$)alkoxy, cyano, (C$_2$–C$_6$)alkynyl, (C$_6$–C$_{10}$)aryl wherein the aryl group is optionally substituted by halo, hydroxy, carboxy, (C$_1$–C$_6$)alkyl, (C$_1$–C$_6$)alkoxy; perfluoro (C$_1$–C$_6$)alkoxy(C$_1$–C$_6$)alkyl or NR$^9$R$^{10}$ wherein R$^9$ and R$^{10}$ are each independently selected from the group consisting of hydrogen, and (C$_1$–C$_6$)alkyl optionally substituted by (C$_1$–C$_6$)alkylpiperidyl, (C$_6$–C$_{10}$) arylpiperidyl, (C$_5$–C$_9$)heteroarylpiperidyl, (C$_6$–C$_{10}$) aryl, (C$_5$–C$_9$)heteroaryl or (C$_3$–C$_6$)cycloalkyl; piperidyl, (C$_1$–C$_6$)alkylpiperidyl, (C$_6$–C$_{10}$) arylpiperidyl, (C$_5$–C$_9$)heteroarylpiperidyl, (C$_1$–C$_6$) arylpiperidyl, (C$_6$–C$_{10}$)aryl, (C$_5$–C$_9$)heteroaryl, (C$_3$–C$_6$)cycloalkyl, R$^{11}$(C$_2$–C$_6$)alkyl, (C$_1$–C$_5$)alkyl (CHR$^{11}$)(C$_1$–C$_6$)alkyl wherein R$^{11}$ is hydroxy, (C$_1$–C$_6$) acyloxy, (C$_1$–C$_6$)alkoxy, piperazino, (C$_1$–C$_6$) acylamino, (C$_1$–C$_6$)alkylthio, (C$_6$–C$_{10}$)arylthio, (C$_1$–C$_6$)alkylsulfinyl, (C$_6$–C$_{10}$)arylsulfinyl, (C$_1$–C$_6$) alkylsulfoxyl, (C$_6$–C$_{10}$)arylsulfoxyl, amino, (C$_1$–C$_6$) alkylamino, ((C$_1$–C$_6$)alkyl)$_2$amino, (C$_1$–C$_6$) acylpiperazino, (C$_1$–C$_6$)alkylpiperazino, (C$_6$–C$_{10}$)aryl (C$_1$–C$_6$)alkylpiperazino, (C$_5$–C$_9$)heteroaryl(C$_1$–C$_6$) alkylpiperazino, morpholino thiomorpholino, piperidino or pyrrolidino; R$^{12}$(C$_1$–C$_6$)alkyl, (C$_1$–C$_5$) alkyl(CHR$^{12}$)(C$_1$–C$_6$)alkyl wherein R$^{12}$ is piperidyl or (C$_1$–C$_6$)alkylpiperidyl; and CH(R$^{13}$)COR$^{14}$ wherein R$^{14}$ is as defined below and R$^{13}$ is hydrogen, (C$_1$–C$_6$) alkyl, (C$_6$–C$_{10}$)aryl(C$_1$–C$_6$)alkyl, (C$_5$–C$_9$)heteroaryl (C$_1$–C$_6$)alkyl, (C$_1$–C$_6$)alkylthio(C$_1$–C$_6$)alkyl, (C$_6$–C$_{10}$) arylthio (C$_1$–C$_6$)alkyl, (C$_1$–C$_6$)alkylsulfinyl(C$_1$–C$_6$)

alkyl, $(C_6-C_{10})$arylsulfinyl$(C_1-C_6)$alkyl, $(C_1C_6)$ alkylsulfonyl$(C_1-C_6)$alkyl, $(C_6-C_{10})$arylsulfonyl $(C_1-C_6)$alkyl, hydroxy$(C_1-C_6)$alkyl, amino$(C_1-C_6)$ alkyl, $(C_1-C_6)$alkylamino$(C_1-C_6)$alkyl, $((C_1-C_6)$ alkylamino$)_2(C_1-C_6)$alkyl, $R^{15}R^{16}NCO(C_1-C_6)$alkyl or $R^{15}OCO(C_1-C_6)$alkyl wherein $R^{15}$ and $R^{16}$ are each independently selected from the group consisting of hydrogen, $(C_1-C_6)$alkyl, $(C_6-C_{10})$aryl$(C_1-C_6)$alkyl and $(C_5-C_9)$heteroaryl $(C_1-C_6)$alkyl; and $R^{14}$ is $R^{17}$ or $R^{17}R^{18}N$ wherein $R^{17}$ and $R^{18}$ are each independently selected from the group consisting of hydrogen, $(C_1-C_6)$alkyl, $(C_6-C_{10})$aryl$(C_1-C_6)$alkyl and $(C_5-C_9)$ heteroaryl$(C_1-C_6)$alkyl;

or a group of the formula

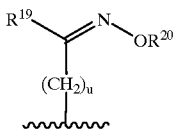

IV wherein u is 0, 1 or 2;

$R^{10}$ is hydrogen, $(C_1-C_6)$alkyl or perfluoro$(C_1-C_6)$alkyl;

$R^{19}$is hydrogen, $(C_1-C_6)$alkyl, $(C_1-C_6)$carboxyalkyl or $(C_6-C_{10})$aryl$(C_1-C_6)$alkyl; or a group of the formula

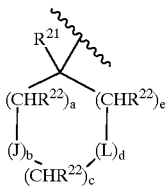

V wherein a is 0, 1 or 2;

b is 0 or 1;

c is 1, 2 or 3;

d is 0 or 1;

e is 0, 1 or 2;

J and L are each independently oxygen or sulfur;

$R^{21}$ is hydrogen, hydroxy, fluoro, $(C_1-C_6)$alkyl, $(C_1-C_6)$ alkoxy, halo$(C_1-C_6)$alkyl, amino, $(C_1-C_6)$acylamino or $NR^{26}R^{27}$ wherein $R^{26}$ and $R^{27}$ are each independently selected from hydrogen, $(C_1-C_6)$alkyl or $(C_6-C_{10})$aryl; and $R^{22}$ is hydrogen, $(C_1-C_6)$alkyl optionally substituted by hydroxy, halo, $(C_1-C_6)$alkylthio, $(C_1-C_6)$alkylsulfinyl or when n is 1 and B and D are both $CR^5$, the two $R^5$groups may be taken together with the carbons to which they are attached to from a group of the formula

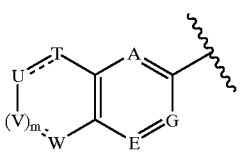

VI wherein the broken lines represent optional double bonds;

m is 0 or 1; and

T, U, V and W are each independently oxygen, sulfur, CO, nitrogen or $CR^5R^6$wherein $R^5$ and $R^6$ are as defined above;

or when A and B, or when n is 1 and B and D, or D and E, or E and G, are both $CR^5$, the two $R^5$ groups may be taken together with the adjacent carbons to which they are attached to form a $(C_5-C_6)$cycloalkyl group optionally substituted by hydroxy or a benzo group;

or when n is 1 and D and E are both $CR^5$, the two $R^5$ groups may be taken together with the adjacent carbons to which they are attached to form a group of the formula

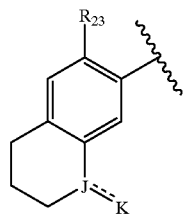

VII wherein the broken line represents an optional double bond;

$R^{23}$ is hydrogen, $(C_1-C_6)$alkyl, halo, amino or $(C_1-C_6)$ alkoxy;

J is C or SO;

K is oxygen, $NR^{24}$ wherein $R^{24}$ is hydroxy, $(C_1-C_6)$ alkoxy or $(C_6-C_{10})$aryl$(C_1-C_6)$alkoxy; or hydroxy;

or $R^{25}SO_2$ wherein $R^{25}$ is defined as $R^1$ above or $(C_3-C_7)$ cycloalkylamino;

$R^2$ is a group of the formula

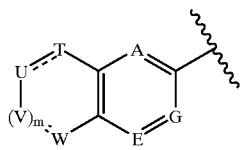

VI wherein the broken lines represent optional double bonds;

m is 0 or 1; and

T, U, V and W are each independently oxygen, sulfur, CO, nitrogen or $CR^5R^6$; and with the proviso that the groups of formulas II and VI cannot have two oxygens, two sulfurs or an oxygen and sulfur defined in adjacent positions;

with the proviso that $R^2$ must be aromatic;

with the proviso that when either a or e is 0, the other must be 1;

with the proviso that when b and d are 1, the sum of a, c and e cannot be 6 or 7; and with the proviso that when A, B, D, E, G, T, U, V and W represent an $sp^2$ carbon, $R^6$ does not exit.

2. A compound according to claim 1 wherein $R^1$ is a group of the formula

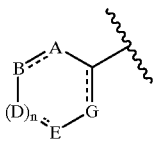
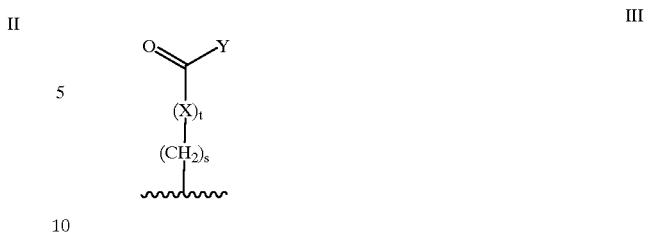

wherein the broken lines represent optional double bonds;

n is 0, 1, 2 or 3;

A, B, D, E and G are each independently oxygen, sulfur, nitrogen or $CR^5R^6$ wherein $R^5$ and $R^6$ are each independently selected from hydrogen, $(C_1-C_6)$alkyl optionally substituted by one or two groups selected from $(C_1-C_6)$alkylamino, $(C_1-C_6)$alkylthio, $(C_1-C_6)$alkoxy, hydroxy, cyano, perfluoro$(C_{1-C6})$alkyl, $(C_{6-C10})$aryl, $(C_{5-C9})$heteroaryl, $(C_{5-C10})$arylamino, $(C_{6-C10})$arylthio, $(C_{6-C10})$aryloxy wherein the aryl group is optionally substituted by $(C_1-C_6)$alkoxy, $(C_1-C_6)$acyl, carboxy, hydroxy or halo; $(C_5-C_9)$heteroarylamino, $(C_5-C_9)$heteroarylthio, $(C_5-C_9)$heteroaryloxy, $(C_6-C_{10})$aryl$(C_6-C_{10})$aryl, $(C_3-C_6)$cycloalkyl, hydroxy, piperazinyl, $(C_6-C_{10})$aryl$(C_1-C_6)$alkoxy, $(C_5-C_9)$heteroaryl$(C_1-C_6)$alkoxy, $(C_1-C_6)$acylamino, $(C_1-C_6)$acylthio, $(C_1-C_6)$acyloxy, $(C_1-C_6)$alkylsulfinyl, $(C_6-C_{10})$arylsulfinyl, $(C_1-C_6)$alkylsulfonyl, $(C_6-C_{10})$arylsulfonyl, amino, $(C_1-C_6)$alkylamino or $((C_1-C_6)$alkyl$)_2$amino; halo, cyano, amino, hydroxy, perfluoro$(C_1-C_6)$alkyl, perfluoro$(C_1-C_6)$alkoxy, $(C_2-C_6)$alkenyl, carboxy$(C_2-C_6)$alkenyl, $(C_2-C_6)$alkynyl, $(C_1-C_6)$alkylamino, $((C_1-C_6)$alkyl$)_2$amino, $(C_1-C_6)$alkylsulfonylamido, $(C_1-C_6)$alkylsulfinyl, aminosulfonyl, $(C_1-C_5)$alkylaminosulfonyl, $((C_1-C_6)$alkyl$_2$aminosulfonyl, $(C_1-C_6)$alkylthio, $(C_1-C_6)$alkoxy, perfluoro$(C_1-C_6)$alkyl, $(C_6-C_{10})$aryl, $(C_5-C_9)$heteroaryl, $(C_6-C_{10})$arylamino, $(C_6-C_{10})$arylthio, $(C_6-C_{10})$aryl$(C_1-C_6)$alkoxy, $(C_5-C_9)$heteroarylamino, $(C_5-C_9)$heteroarylthio, $(C_5-C_9)$heteroaryloxy, $(C_3-C_6)$cycloalkyl, $(C_1-C_6)$alkyl(hydroxymethylene), piperidyl, pyridinyl, thienyl, furanyl, $(C_1-C_6)$alkylpiperidyl, $(C_1-C_6)$acylamino, $(C_1-C_6)$acylthio, $(C_1-C_6)$acyloxy and $R^7(C_1-C_6)$ alkyl wherein $R^7$ is $(C_1-C_6)$acylpiperazino, $(C_6-C_{10})$arylpiperazino, $(C_5-C_9)$heteroarylpiperazino, $(C_1-C_6)$alkylpiperazino, $(C_6-C_{10})$aryl$(C_1-C_6)$alkylpiperazino, $(C_5-C_9)$heteroaryl$(C_1-C_6)$alkylpiperazino, morpholino, thiomorpholino, piperidino, pyrrolidino, piperidyl, $(C_1-C_6)$alkylpiperidyl, $(C_6-C_{10})$arylpiperidyl, $(C_5-C_9)$heteroarylpiperidyl, $(C_1-C_6)$alkylpiperidyl$(C_1-C_6)$alkyl, $(C_6-C_{10})$arylpiperidyl$(C_1-C_6)$alkyl, $(C_5-C_9)$heteroarylpiperidyl$(C_1-C_6)$alkyl or $(C_1-C_6)$acylpiperidyl.

3. A compound according to claim 2 wherein at least one of said $R^5$ or $R^6$ groups of said $R^1$ must be a group of the formula where s is 0 to 6;

t is 0 or 1;

X is oxygen or $NR^8$ wherein $R^8$ is hydrogen, $(C_1-C_6)$alkyl or $(C_3-C_7)$cycloalkyl$(C_1-C_6)$alkyl;

Y is hydrogen, hydroxy, $(C_1-C_6)$alkyl, optionally substituted by halo, hydroxy or cyano; $(C_1-C_6)$alkoxy, cyano, $(C_2-C_6)$alkynyl, $(C_6-C_{10})$aryl wherein the aryl group is optionally substituted by halo, hydroxy, carboxy, $(C_1-C_6)$alkyl, $(C_1-C_6)$alkoxy; perfluoro $(C_1-C_6)$alkyl, $(C_1-C_6)$alkoxy$(C_1-C_6)$alkyl or $NR^9R^{10}$ wherein $R^9$ and $R^{10}$ are each independently selected from the group consisting of hydrogen, and $(C_1-C_6)$ alkyl optionally substituted by $(C_1-C_6)$alkylpiperidyl, $(C_6-C_{10})$arylpiperidyl, $(C_5-C_9)$heteroarylpiperidyl, $(C_6-C_{10})$aryl, $(C_5-C_9)$heteroaryl or $(C_3-C_6)$cycloalkyl; piperidyl, $(C_1-C_6)$alkylpiperidyl, $(C_6-C_{10})$arylpiperidyl, $(C_5-C_9)$heteroarylpiperidyl, $(C_1-C_6)$acylpiperidyl, $(C_6-C_{10})$aryl, $(C_5-C_9)$heteroaryl, $(C_3-C_6)$cycloalkyl, $R^{11}(C_2-C_6)$alkyl, $(C_1-C_5)$alkyl $(CHR^{11})(C_1-C_6)$alkyl wherein $R^{11}$ is hydroxy, $(C_1-C_6)$acyloxy, $(C_1-C_6)$alkoxy, piperazino, $(C_1-C_6)$acylamino, $(C_1-C_6)$alkylthio, $(C_6-C_{10})$arylthio, $(C_1-C_6)$alkylsulfinyl, $(C_6-C_{10})$arylsulfinyl, $(C_1-C_6)$alkylsulfoxyl, $(C_6-C_{10})$arylsulfoxyl, amino, $(C_1-C_6)$alkylamino, $((C_1-C_6)$alkyl$)_2$amino, $(C_1-C_6)$acylpiperazino, $(C_1-C_6)$alkylpiperazino, $(C_6-C_{10})$aryl $(C_1-C_6)$alkylpiperazino, $(C_5-C_9)$heteroaryl$(C_1-C_6)$alkylpiperazino, morpholino, thiomorpholino, piperidino or pyrrolidino; $R^{12}(C_1-C_6)$alkyl$(C_1-C_5)$ $(CHR^{12})(C_1-C_6)$alkyl wherein $R^{12}$ is piperidyl or $(C_1-C_6)$alkylpiperidyl; and $CH(R^{13})COR^{14}$ wherein $R^{14}$ is as defined below and $R^{13}$ is hydrogen, $(C_1-C_6)$alkyl, $(C_6-C_{10})$aryl$(C_1-C_6)$alkyl, $(C_5-C_9)$heteroaryl $(C_1-C_6)$alkyl, $(C_1-C_6)$alkylthio$(C_1-C_6)$alkyl, $(C_6-C_{10})$arylthio$(C_1-C_6)$alkyl, $(C_1-C_6)$alkylsulfinyl$(C_1-C_6)$alkyl, $(C_6-C_{10})$arylsulfinyl$(C_1-C_6)$alkyl, $(C_1-C_6)$alkylsulfonyl$(C_1-C_6)$alkyl, $(C_6-C_{10})$arylsulfonyl $(C_1-C_6)$alkyl, hydroxy$(C_1-C_6)$alkyl, amino $(C_1-C_6)$alkyl, $(C_1-C_6)$alkylamino$(C_1-C_6)$alkyl, $((C_1-C_6)$alkylamino$)_2(C_1-C_6)$alkyl, $R^{15}R^{16}NCO(C_1-C_6)$alkyl or $R^{15}OCO(C_1-C_6)$alkyl wherein $R^{15}$ and $R^{16}$ are each independently selected from the group consisting of hydrogen, $(C_1-C_6)$alkyl, $(C_6-C_{10})$aryl$(C_1-C_6)$alkyl and $(C_5-C_9)$heteroaryl$(C_1-C_6)$alkyl; and $R^{14}$ is $R^{17}O$ or $R^{17}R^{18}N$ wherein $R^{17}$ and $R^{18}$ are each independently selected from the group consisting of hydrogen, $(C_1-C_6)$alkyl, $(C_6-C_{10})$aryl$(C_1-C_6)$alkyl and $(C_5-C_9)$heteroaryl$(C_1-C_6)$alkyl.

4. A compound according to claim 2 wherein at least one of said $R^5$ or $R^6$ groups of said $R^1$ must be a group of the formula

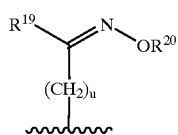

IV wherein u is 0, 1 or 2;

R$^{19}$ is hydrogen, (C$_1$–C$_6$)alkyl or perfluoro(C$_1$–C$_6$)alkyl; and

R$^{20}$ is hydrogen, (C$_1$–C$_6$)alkyl, (C$_1$–C$_6$)carboxyalkyl or (C$_6$–C$_{10}$)aryl(C$_1$–C$_6$)alkyl.

5. A compound according to claim 2 wherein at least one of said R$^5$ or R$^6$ groups of said R$^1$ must be a group of the formula

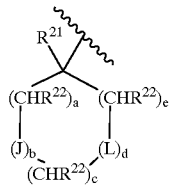

V wherein a is 0, 1 or 2;

b is 0 or 1;

c is 1, 2 or 3;

d is 0 or 1;

e is 0, 1 or 2 ;

J and L are each independently oxygen or sulfur;

R$^{21}$ is hydrogen, hydroxy, fluoro, (C$_1$–C$_6$)alkyl, (C$_1$–C$_6$)alkoxy, halo (C$_1$–C$_6$)alkyl, amino (C$_1$–C$_6$)acylamino or NR$^{26}$R$^{27}$wherein R$^{26}$ and R$^{27}$ are each independently selected from hydrogen, (C$_1$–C$_6$)alkyl or (C$_6$–C$_{10}$)aryl; and R$^{22}$ is hydrogen, (C$_1$–C$_6$)alkyl optionally substituted by hydroxy, halo, (C$_1$–C$_6$)alkylthio, (C$_1$–C$_6$)alkylsulfinyl or (C$_1$–C$_6$)alkylsulfonyl.

R$^{22}$is hydrogen, (C$_1$–C$_6$)alkyl optionally substituted by hydroxy, halo, (C$_1$–C$_6$)alkylthio, (C$_1$–C$_6$)alkylsulfinyl or (C$_1$–C$_6$)alkylsulfonyl.

6. A compound according to claim 1 wherein R$^1$ is a group of the formula

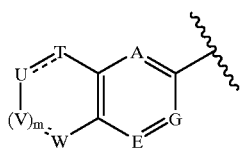

VI wherein the broken lines represent optional double bonds;

m is 0 or 1; and

T, U, V and W are each independently oxygen, sulfur, CO, nitrogen or CR$^5$R$^6$ wherein R$^5$ and R$^6$ are as defined in claim 1.

7. A compound according to claim 1 wherein R$^1$ is a group of the formula

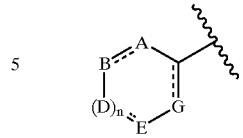

II wherein A and B, or wherein n is 1 and B and D, or D and E, or E and G, are both CR$^5$ , the two R$^5$ groups may be taken together with the adjacent carbons to which they are attached to form a (C$_5$–C$_6$)cycloalkyl group optionally substituted by hydroxy or a benzo group.

8. A compound according to claim 1 wherein R$^1$ is a group of the formula

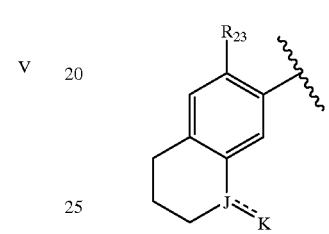

VII wherein the broken line represents an optional double bond;

R$^{23}$ is hydrogen, (C$_1$–C$_6$)alkyl, halo, amino or (C$_1$–C$_6$) alkoxy;

J is C or SO; and

K is oxygen, NR$^{24}$ wherein R$^{24}$ is hydroxy, (C$_1$–C$_6$) alkoxy or (C$_6$–C$_{10}$)aryl(C$_1$–C$_6$)alkoxy; or hydroxy; or R$^{25}$SO$_2$ wherein R$^{25}$ is defined as R$^1$ in claim 1 or (C$_3$–C$_7$)cycloalkylamino.

9. A compound according to claim 1, wherein R$^1$ is a group of the formula

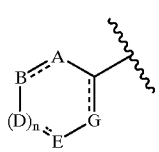

II wherein the broken lines represent double bond;

n is 0 is 1;

A is CR$^5$ wherein R$^5$ is hydrogen or halo;

B and E are both independently CR$^5$ wherein R$^5$ is hydrogen cyano, halo, (C$_1$–C$_6$) alkyl optionally substituted by one or two hydroxy; (C$_3$–C$_7$) cycloalkylaminosulfonyl, (C$_1$–C$_6$)alkylaminosulfonyl, or a group of the formula

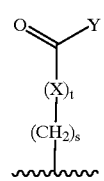

III wherein s is 0;

t is 0; and

Y is hydrogen, $(C_1-C_6)$alkyl optionally substituted by halo; or $(C_1-C_6)$alkoxy$(C_1-C_6)$alkyl;

or a group of the formula

V wherein a is 0 or 1;
b is 0 or 1;
c is 1 or 2;
d is 0 or 1;
e is 0 or 1;
J and L are each independently oxygen or sulfur;
$R^{21}$ is hydrogen, hydroxy or $(C_1-C_6)$alkyl optionally substituted by halo; and
$R^{22}$ is hydrogen or $(C_1-C_6)$alkyl optionally substituted by hydroxy, halo, $(C_1-C_6)$alkylthio, $(C_1-C_6)$alkylsulfinyl or $(C_1-C_6)$alkylsulfonyl;

IV wherein u is 0 or 1;
$R^{19}$ is $(C_1-C_6)$alkyl or trifluoromethyl; and
$R^{20}$ is hydrogen;
D is $CR^5$ wherein $R^5$ is hydrogen, $(C_{1-C6})$alkyl or halo;
G is $CR^5$ wherein $R^5$ is oxygen, sulfur or $CR^5$ wherein $R^5$ is hydrogen or halo; or when n is 1 and B and D are both $CR^5$, the two $R^5$ groups may be taken together with he carbons to which they are attached to from a group of the formula

VI wherein the broken lines represent double bonds;
m is 0;
T is oxygen, nitrogen or $CR^5$ wherein $R^5$ is hydrogen;
U is CO or $CR^5$ wherein $R^5$ is hydrogen; and
W is nitrogen or $CR^5$ wherein $R^5$ is hydrogen;
or when n is 1 and D and E are both $CR^5$, the two $R^5$ groups may be taken together with the adjacent carbons to which they are attached to from a group of the formula

VII wherein the broken line represents an optional double bond;
$R^{23}$ is hydrogen or $(C_1-C_6)$alkyl;
J is C or SO
K is oxygen, $NR^{24}$, wherein $R^{24}$ is hydroxy; or hydroxy.
10. A compound according to claim 1, wherein said compound is selected from the group consisting of:

1-(4-Chloro-2,6-diisopropyl-phenyl)-3-[3-(1-hydroxy-1-methyl-ethyl)-benzenesulfonyl]-urea;

1-(1,2,3,5,6,7-Hexahydro-s-indacen-4-yl)-3-[4-(1-hydroxy-1-methyl-ethyl)-furan-2-sulfonyl]-urea;

1-(1,2,3,5,6,7-Hexahydro-4-aza-s-indacen-8-yl)-3-[4-(1-hydroxy-1-methyl-ethyl)-furan-2-sulfonyl]-urea;

1-(1,2,3,5,6,7-Hexahydro-s-indacen-4-yl)-3-[4-(1-hydroxy-1-methyl-ethyl)-thiophene-2-sulfonyl]-urea;

1-(4-[1,3]Dioxolan-2-yl-furan-2-sulfonyl)-3-(1,2,3,5,6,7-hexahydro-s-indacen-4-2yl)-urea;

1-(2,6-Diisopropyl-phenyl)-3-[4-(1-hydroxy-1-methyl-ethyl)-furan-2-sulfonyl]-urea;

1-(2,6-Diisopropyl-phenyl)-3-[4(1-hydroxy-1-methyl-ethyl)-thiophene-2-sulfonyl]-urea;

1-(4-Acetyl-thiophene-2-sulfonyl)-3-(1,2,3,5,6,7-hexahydro-s-indacen-4-yl)-urea;]

1-(1H-Benzoimidazole-5-sulfonyl)-3-(1,2,3,5,6,7-hexahydro-s-indacen-4-yl)-urea;

[1-(1,2,3,5,6,7-Hexahydro-s-indacen-4yl)-3-[4-(1-hydroxy-1-methyl-ethyl)-thiophene-2-sulfonyl]-urea;

1-(8-Chloro-1,2,3,5,6,7-hexahydro-s-indacen-4-yl)-3-[4-(1-hydroxy-1-methyl-ethyl)-furan-2-sulfonyl]-urea;

1-(4-Acetyl-furan-2-sulfonyl)-3-(1,2,3,5,6,7-hexahydro-s-indacen-4-yl)-urea;

1-(8-fluoro-1,2,3,5,6,7-hexahydro-s-indacen-4-yl)-3-[4-(1-hydroxy-1-methyl-ethyl)-furan-2-sulfonyl]-urea;

1-(4-Fluoro-2,6-diisopropyl-phenyl)-3-[3(1-hydroxy-1-methyl-ethyl)-benzenesulfonyl]-urea;]

1(6-Fluoro-1H-benzoimidazole-5-sulfonyl)-3-(1,2,3,5,6,7-hexahydro-s-indacen-4-yl)-urea and[;

1-(4-Chloro-2,6-diisopropyl-phenyl)-3-(1H-indole-6-sulfonyl)-urea;

1-(4-Chloro-2,6-diisopropyl-phenyl)-3-(5-fluoro-1H-indole-6-sulfonyl)-urea;

1 [1,2,3,5,6,7-Hexahydro-s-indacen-u-yl)-3-(1H-indole-6-sulfonyl)-urea;]

1-(5-Fluoro-1H-indole-6-sulfonyl)-3-(1,2,3,5,6,7-hexanhydro-5-indacen-4)-urea;

[1-[4-Chloro-2,6-diisopropyl-phenyl]-3[2fluoro-5-(2methyl-(1,3)dioxolan-2-yl)-benzenesulfonyl]-urea;

3-[3-[4-Chloro-2,6-diisopropyl-phenyl]-ureidosulfonyl]-N-methyl-benzenesulfonamide;

1-[2-Fluoro-5-(2-methyl-(1,3)dioxolan-2-yl)benzenesulfonyl]-3-1,2,3,5,6,7-hexahydro-indacen-4-yl)-urea; and 3-[3-(1,2,3,5,6,7-Hexahydro-S-indacen-4-yl)-ureidosulfonyl]-N-methyl-benzenesulfonamide].

11. A pharmaceutical composition for the treatment of meningitis and salpingitis, septic chock, disseminated intravascular coagulation, and/or adult respiratory distress syndrome, acute or chronic inflammation, arthritis, cholangitis, colitis, encephalitis, endocarditis, glomerulonephritis, hepatitis, myocarditis, pancreatitis, pericarditis, reperfusion injury, vasculitis, acute and delayed hypersensitivity, graft rejection, and graft-versus-host disease, auto-immune disease [including Type 1 diabetes mellitus and multiple sclerosis], periodonate diseases, interstitial pulmonary fibrosis, cirrhosis, systemic sclerosis, keloid formation, tumors which products IL-1 as an autocrine growth factor, cachexia, Alzheimer's disease, percussion injury, depression, atherosclerosis and osteoporosis in a mammal, [including a human], comprising administering an amount of a compound of claim 1 or a pharmaceutically acceptable salt thereof, effective in such treatments or inhibition and a pharmaceutically acceptable carrier.

12. A method for treating a condition selected from the group consisting of meningitis and salpingitis, septic shock, disseminated intravascular coagulation, and/or adult respiratory distress syndrome, acute or chronic inflammation, arthritis, cholangitis, colitis, encephalitis, endocarditis, glomerulonephritis, hepatitis, myocarditis, pancreatitis, pericarditis, reperfusion injury, vasculitis, acute and delayed hypersensitivity, graft rejection, and graft-versus-host disease, auto-immune disease [including Type 1 diabetes mellitus and multiple sclerosis], periodonate diseases, interstitial pulmonary fibrosis, cirrhosis, systemic sclerosis, keloid formation, tumors which produce IL-1as an autocrine growth factor, cachexia, Alzheimer's disease percussion injury, depression, atherosclerosis and osteoporosis in a mammal, [including a human], comprising administering to said mammal an amount of a compound of claim 1 or a pharmaceutically acceptable salt thereof, effective in treating such a condition.

13. The compound 4-(1-hydroxy-1-methyl-ethyl)-furan-2-sulfonamide.

* * * * *